US011739305B2

(12) United States Patent
Chen et al.

(10) Patent No.: US 11,739,305 B2
(45) Date of Patent: Aug. 29, 2023

(54) SIALYLTRANSFERASE VARIANTS HAVING NEOSIALIDASE ACTIVITY

(71) Applicant: The Regents of the University of California, Oakland, CA (US)

(72) Inventors: Xi Chen, Davis, CA (US); John B. McArthur, Davis, CA (US); Andrew J. Fisher, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/955,737

(22) PCT Filed: Dec. 21, 2018

(86) PCT No.: PCT/US2018/067290

§ 371 (c)(1),
(2) Date: Jun. 18, 2020

(87) PCT Pub. No.: WO2019/126749

PCT Pub. Date: Jun. 27, 2019

(65) Prior Publication Data

US 2020/0325457 A1 Oct. 15, 2020

Related U.S. Application Data

(60) Provisional application No. 62/609,310, filed on Dec. 21, 2017.

(51) Int. Cl.

| | |
|---|---|
| ***C12N 9/10*** | (2006.01) |
| ***C12N 1/21*** | (2006.01) |
| ***C12N 15/70*** | (2006.01) |
| ***C12N 15/63*** | (2006.01) |

(52) U.S. Cl.

CPC .......... *C12N 9/1081* (2013.01); *C12N 15/63* (2013.01); *C12Y 204/99001* (2013.01); *C12Y 204/99004* (2013.01)

(58) Field of Classification Search

None

See application file for complete search history.

(56) References Cited

U.S. PATENT DOCUMENTS

| | | | |
|---|---|---|---|
| 9,481,902 | B2 | 11/2016 | Czabany et al. |
| 2016/0177275 | A1 | 6/2016 | Chen et al. |
| 2017/0204381 | A1 | 7/2017 | Chen et al. |

OTHER PUBLICATIONS

Singh et al., Curr. Protein Pept. Sci. 18:1-11, 2017 (Year: 2017).*
Zhang et al., Structure 26:1474-1485, 2018 (Year: 2018).*
Yamamoto et al., J. Biochem. 123:94-100, 1998 (Year: 1998).*
Xu et al., ACS Catal. 8:7222-7227, Jul. 2018 (Year: 2018).*
Schultz et al., Proteins Structure and Function, pp. 521-528, Plenum Press, New York, 1987 (Year: 1987).*
Chothia, C., Ann. Rev. Biochem. 53:537-572, 1984 (Year: 1984).*
International Search Report and Written Opinion in PCT/US2018/067290 dated Apr. 8, 2019; 10 pages.
Cheng, J et al.; "Trans-sialidase activity of *Photobacterium damsela* alpha2,6-sialyltransferase and its application in the synthesis of sialosides"; *Glycobiology*; vol. 20, No. 2; Oct. 30, 2009; pp. 260-268.
McArthur, J.B. et al.; "alpha2-6-Neosialidase: A Sialyltransferase Mutant as a Sialyl Linkage-Specific Sialidase"; *ACS Chemical Biology*; vol. 13, Issue 5; Mar. 15, 2018; pp. 1228-1234.

* cited by examiner

*Primary Examiner* — David Steadman
(74) *Attorney, Agent, or Firm* — Kilpatrick Townsend and Stockton LLP

(57) ABSTRACT

α2-6-Sialyltransferase (2,6ST) variants having improved α2-6-specific sialidase activity as compared to the native 2,6ST enzymes are described. The variants include GT80 sialyltransferases such as *P. damselae* Pd2,6ST. Methods for making de-sialylated products and screening sialidase activity are also described.

7 Claims, 5 Drawing Sheets

Specification includes a Sequence Listing.

Neu5Aca2-6GalbX (1)

X-Gal or GalbX 5,5'-Dibromo-4,4'-dichloro-indigo
Blue precipitate (Blue colony)

Neu5Acα2–6GalβpNP (2)

Kdnα2–6GalβpNP (5)

Neu5Acα2–3GalβpNP (3)

Neu5Gcα2–6GalβpNP (6)

Neu5Acα2–8Neu5Acα2–3GalβpNP (4)

Neu5Acα2–6GalNAcβpNP (7)

SIALYLTRANSFERASE VARIANTS HAVING NEOSIALIDASE ACTIVITY

CROSS-REFERENCES TO RELATED APPLICATIONS

The present application is a US National Phase Application Under 371 of PCT/US2018/067290, filed Dec. 21, 2018, which claims priority to U.S. Provisional Pat. Appl. No. 62/609,310, filed on Dec. 21, 2017, which applications are incorporated herein by reference in their entireties.

STATEMENT AS TO RIGHTS TO INVENTIONS MADE UNDER FEDERALLY SPONSORED RESEARCH AND DEVELOPMENT

This invention was made with Government support under Grant Nos. R01A1130684 and R01HD065122, awarded by the National Institutes of Health. The Government has certain rights in the invention.

REFERENCE TO SUBMISSION OF A SEQUENCE LISTING AS A TEXT FILE

The Sequence Listing written in file 076916-217820US-1199034_SL.txt created on Jun. 15, 2020, 25,952 bytes, machine format IBM-PC, MS-Windows operating system, is hereby incorporated by reference in its entirety for all purposes.

BACKGROUND OF THE INVENTION

Sialidases are crucial tools for the structural and functional characterization of sialic acid-containing carbohydrates and glycoconjugates, including those presented in cellular extracts and physiological fluids, on cellular surfaces and in tissues. Sialidase treatment provides a convenient method for determining the presence of sialic acids, and it is mild enough to be useful for the functional evaluation of sialic acids on sensitive biological samples. For example, glycoproteins treated with a sialidase were rapidly cleared to the liver upon intravenous injection in rabbits, leading to the discovery that terminal sialic acids are critically important to the half-life of circulating therapeutic glycoproteins. Similarly, α2-3-selective sialidase treatment of lymphoid organ samples eliminated binding of mouse lymphocytes to the peripheral lymph node high endothelial venules, providing the first evidence that the endogenous ligands of L-selectin contained terminal α2-3-linked sialic acid. Sialidase treatment has also been used to enhance the immunogenicity of conjugated vaccines prepared from group B *Streptococcus* type V capsular polysaccharide, producing robust protection against lethal challenge by live group B *Streptococcus* in neonatal mice.

Although powerful and broadly useful for the study or modification of carbohydrates, known sialidases possess either specificity toward α2-3-linked sialic acid or a broad promiscuity towards sialic acid with α2-3-, α2-6-, and α2-8-linkages. The lack of α2-6-linkage specific sialidases in the toolbox limits the functional studies of sialic acid-containing biomolecules. We aim to obtain a highly active, α2-6-linkage-specific sialidase with promiscuity in cleaving various sialic acid forms.

Previously we have shown that several bacterial sialyltransferases including those in the Carbohydrate Active Enzyme (CAZy) glycosyltransferase GT80 and GT54 families display linkage-specific sialidase and donor hydrolysis activities, although such activities were much lower than their glycosyltransferase activities. Recently, Withers et al. showed that these types of sialidase activities require cytidine 5'-monophosphate (CMP) and suggested a two-step mechanism beginning with the cleavage of the sialosidic linkage in the presence of CMP by a reverse sialyltransferase reaction to form CMP-sialic acid, followed by a forward sialyltransferase reaction using water as the acceptor substrate to form CMP and sialic acid (donor hydrolysis). Described herein in the use of enzyme engineering to improve this "neosialidase" activity of *Photobacterium damselae* α2-6-sialyltransferase (Pd2,6ST) to useful rates while retaining its sialyl-linkage specificity.

BRIEF SUMMARY OF THE INVENTION

Provided herein are α2-6-sialyltransferase (2,6ST) variants having improved α2-6-specific sialidase activity as compared to the native 2,6ST enzymes. In some embodiments, the sialyltransferase variant is engineered from a GT80 sialyltransferase such as *P. damselae* Pd2,6ST. Nucleic acids, vectors, and host cells for expression of the 2,6ST variants are also provided.

Also provided herein are methods for making de-sialylated products. The methods include forming a reaction mixture containing a sialoside and a 2,6ST variant, and maintaining the reaction mixture under conditions sufficient to remove the sialic acid moiety from the sialoside, thereby forming the de-sialylated product.

Also provided herein are methods for detecting sialidase activity in host cells. The methods include:

(i) culturing a host cell under conditions sufficient to express a target sialidase in the host cell, wherein the host cell also expresses β-galactosidase;

(ii) combining the cultured cells from step (i) with a compound according to Formula I under conditions sufficient to form an indigo product in the presence of the target sialidase and the β-galactosidase (I)

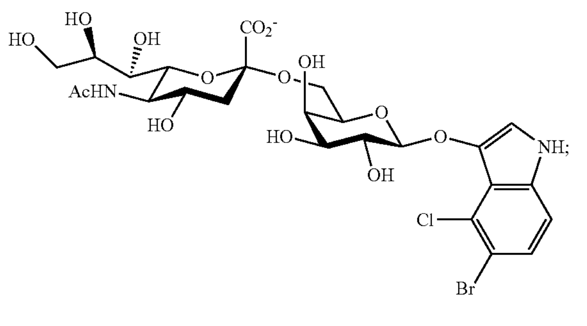

and (iii) detecting the sialidase activity in the host cell by detecting a blue color in the host cell due to formation of the indigo product.

DETAILED DESCRIPTION OF THE INVENTION

Figure 1:
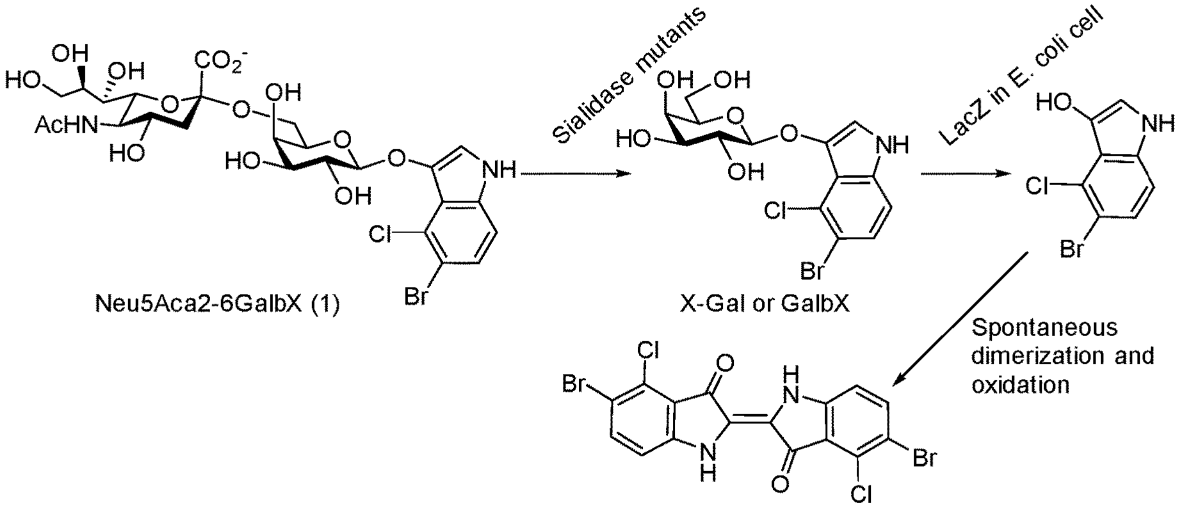
FIG. 1 shows a schematic depiction of high-throughput α2-6-sialidase activity screening, using LacZ-containing *E. coli* cells expressing sialidase mutants.

Described herein is a high-throughput blue-white colony sialidase activity screening method to identify sialyltransferases such as Pd2,6ST mutants with improved α2-6-specific sialidase activity from mutant libraries generated by sequential saturation mutagenesis. Improved sialidases, including a Pd2,6ST neosialidase triple mutant (S232L/T356S/W361F) with 101-fold improved α2-6-sialidase activity, are provided. These enzyme variants, termed neosialidases, exhibit high selectivity for α2-6-sialyl linkages and are active toward two common sialic acid forms N-acetylneuraminic acid (Neu5Ac) and N-glycolylneuraminic acid (Neu5Gc), among others. The neosialidases are valuable tools for complementing α2-3-specific and sialyl linkage promiscuous sialidases for sialoglycan structural analysis and functional characterization. Moreover, the sequential saturation mutagenesis and screening strategy described herein can be explored to evolve other substrate linkage specific neoglycosidases from the corresponding glycosyltransferases.

I. DEFINITIONS

The terms "peptide," "polypeptide," and "protein" are used interchangeably herein to refer to a polymer of amino acid residues. All three terms apply to naturally occurring amino acid polymers and non-natural amino acid polymers, as well as to amino acid polymers in which one (or more) amino acid residue is an artificial chemical mimetic of a corresponding naturally occurring amino acid. As used herein, the terms encompass amino acid chains of any length, including full-length proteins, wherein the amino acid residues are linked by covalent peptide bonds.

The term "sialyltransferase" refers to an enzyme that catalyzes the transfer of a sialic acid moiety from a sialic acid donor (e.g., a sialic acid nucleotide donor) to an acceptor such as an oligosaccharide, a polysaccharide, or a glycosylated protein.

The term "sialidase" refers to an enzyme that catalyzes the removal of a sialic acid moiety from a sialylated glycoside such as a sialylated oligosaccharide, a sialylated polysaccharide, or a sialylated glycoprotein.

As used herein, the term "sialic acid" refers to N- and O-substituted derivatives of neuraminic acid (i.e., N- and O-substituted derivatives of 5-amino-2-keto-3,5-dideoxy-D-glycero-D-galactononulosonic acid—also referred to as (4S,5R,6R,7S,8R)-5-amino-4,6,7,8,9-pentahydroxy-2-oxo-nonanoic acid). Sialic acids include, but are not limited to, N-acetylneuraminic acid (Neu5Ac), N-glycolylneuraminic acid (Neu5Gc), and 2-keto-3-deoxy-D-glycero-D-galac-tonononic acid (KDN), as well as amino, azido, deoxy, O-acetyl, O-lactyl, O-methyl, O-sulfate and O-phosphate derivatives.

The terms "mutant" and "variant," in the context of the enzymes disclosed herein, mean a polypeptide, typically recombinant, that comprises one or more amino acid substitutions relative to a corresponding, naturally-occurring or unmodified sialyltransferase.

The term "amino acid" refers to any monomeric unit that can be incorporated into a peptide, polypeptide, or protein. Amino acids include naturally-occurring α-amino acids and their stereoisomers, as well as unnatural (non-naturally occurring) amino acids and their stereoisomers. "Stereoisomers" of a given amino acid refer to isomers having the same molecular formula and intramolecular bonds but different three-dimensional arrangements of bonds and atoms (e.g., an L-amino acid and the corresponding D-amino acid).

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either the commonly known three letter symbols or by the one-letter symbols recommended by the IUPAC-IUB Biochemical Nomenclature Commission. Nucleotides, as described herein, may also be referred to by their commonly accepted single-letter codes.

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

The terms "amino acid modification" and "amino acid alteration" refer to a substitution, a deletion, or an insertion of one or more amino acids. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains exemplary amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "nucleic acid," "nucleotide," and "polynucleotide" refer to deoxyribonucleic acids (DNA) or ribonucleic acids (RNA) and polymers. The term includes, but is not limited to, single-, double-, or multi-stranded DNA or RNA, genomic DNA, cDNA, and DNA-RNA hybrids, as well as other polymers comprising purine and/or pyrimidine bases or other natural, chemically modified, biochemically modified, non-natural, synthetic, or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)).

The terms "nucleotide sequence encoding a peptide" and "gene" refer to the segment of DNA involved in producing a peptide chain. In addition, a gene will generally include regions preceding and following the coding region (leader and trailer) involved in the transcription/translation of the gene product and the regulation of the transcription/translation. A gene can also include intervening sequences (introns) between individual coding segments (exons). Leaders, trailers, and introns can include regulatory elements that are necessary during the transcription and the translation of a gene (e.g., promoters, terminators, translational regulatory sequences such as ribosome binding sites and internal ribosome entry sites, enhancers, silencers, insulators, boundary elements, replication origins, matrix attachment sites and locus control regions, etc.). A "gene product" can refer to either the mRNA or protein expressed from a particular gene.

"Percentage of sequence identity" is determined by comparing two optimally aligned sequences over a comparison window, wherein the portion of the sequence in the comparison window may comprise additions or deletions (i.e., gaps) as compared to the reference sequence which does not comprise additions or deletions, for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

"Identical" and "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 75%, at least 80%, at least 85%, at least 90%, at least 95%, or at least 99% identical over a specified region), when compared and aligned for maximum correspondence over a comparison window, or designated region as measured using one of the following sequence comparison algorithms or by manual alignment and visual inspection. These definitions also refer to the complement of a nucleic acid test sequence.

"Similarity" and "percent similarity," in the context of two or more polypeptide sequences, refer to two or more sequences or subsequences that have a specified percentage of amino acid residues that are either the same or similar as defined by a conservative amino acid substitutions (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% similar over a specified region), when compared and aligned for maximum correspondence over a comparison window, or designated region as measured using one of the following sequence comparison algorithms or by manual alignment and visual inspection. Sequences are "substantially similar" to each other if, for example, they are at least 20%, at least 25%, at least 30%, at least 35%, at least 40%, at least 45%, at least 50%, or at least 55% similar to each other.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Additional examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see, e.g., Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA,* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or peptides are substantially identical is that the peptide encoded by the first nucleic acid is immunologically cross reactive with the antibodies raised against the peptide encoded by the second nucleic acid. Thus, a peptide is typically substantially identical to a second peptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The terms "transfection" and "transfected" refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88.

The terms "expression" and "expressed" in the context of a gene refer to the transcriptional and/or translational product of the gene. The level of expression of a DNA molecule in a cell may be determined on the basis of either the amount of corresponding mRNA that is present within the cell or the amount of protein encoded by that DNA produced by the cell. Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "promoter," as used herein, refers to a polynucleotide sequence capable of driving transcription of a coding sequence in a cell. Thus, promoters used in the polynucleotide constructs described herein include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "constitutive promoter" is one that is capable of initiating transcription in nearly all tissue types, whereas a "tissue-specific promoter" initiates transcription only in one or a few particular tissue types. An "inducible promoter" is one that initiates transcription only under particular environmental conditions or developmental conditions.

A polynucleotide/polypeptide sequence is "heterologous" to an organism or a second polynucleotide/polypeptide sequence if it originates from a different species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. For example, recombinant cells express genes that are not found within the native (non-recombinant) form of the cell or express native genes that are otherwise abnormally expressed, under-expressed, or not expressed at all.

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition. One of skill will recognize that the inserted polynucleotide sequence need not be identical, but may be only substantially similar to a sequence of the gene from which it was derived.

The terms "vector" and "recombinant expression vector" refer to a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous.

Similarly, certain amino acid sequences that are non-contiguous in a primary polypeptide sequence may nonetheless be operably linked due to, for example folding of a polypeptide

II. ENGINEERED NEOSIALIDASES

Provided herein are α2-6-sialyltransferase (2,6ST) variants, also referred to as neosialidases, having improved α2-6-specific sialidase activity as compared to the native 2,6ST. A native sialyltransferase, having little or no measurable sialidase activity, can be engineered using the methods described herein to provide high levels of sialidase activity. Typically, the activity of the 2,6ST variant in cleaving sialic acid from a sialoside is at least twice as high as the activity of the native 2,6ST in cleaving sialic acid from the sialoside under the same reaction conditions (e.g., at 37° C., pH 6). The sialidase activity level of the 2,6ST variant may be, for example, 5-fold higher, 20-fold higher, 50-fold higher, 100-fold higher, 250-fold higher, 500-fold higher, or 1000-fold higher than the sialidase activity level of the native 2,6ST.

By "α2-6-specific," it is meant that the neosialidases according to the present disclosure demonstrate high efficiency in the cleavage of sialosides containing sialic acids linked via α2,6 glycosidic bonds, as compared to cleavage of sialosides containing sialic acids bonded via other linkages (e.g., via α2,3 glycosidic bonds or α2,8 glycosidic bonds). In some embodiments, the activity of the 2,6ST variant in cleaving an α2,6-linked sialic acid is at least twice as high as the activity of the 2,6ST variant in cleaving an alternatively-linked sialic acid (e.g., an α2,3- or α2,8-linked sialic acid) under the same reaction conditions (e.g., at 37° C., pH 6). The level of α2,6 bond cleavage produced by the 2,6ST variant may be, for example, 5-fold higher, 20-fold higher, 50-fold higher, 100-fold higher, 250-fold higher, 500-fold higher, or 1000-fold higher than the level of α2,3 bond cleavage or α2,8 bond cleavage produced by the 2,6ST variant.

Sialyltransferases are generally understood to catalyze a nucleophilic substitution (single displacement) reaction mechanism that includes the nucleophilic attack of a hydroxyl group of a sialic acid acceptor (e.g., the 6-hydroxyl group of a lactoside acceptor) on the anomeric center of a donor sugar such as CMP-Neu5Ac. A catalytic residue serves as a general base to deprotonate the hydroxyl group of the sialic acid acceptor. The new glycosidic bond is inverted with respect to the donor sugar—a β-linked sialic acid in the donor is α-linked in the final product, or vice versa. Inverting reactions occur via formation of an oxocarbenium-ion transition state and $S_N2$-like departure of the nucleotide leaving group. Catalysis occurs in a closed, active conformation induced by the initial binding of the nucleotide sugar. The closed conformation is thought to help define the acceptor binding site and, by excluding water molecules, to prevent non-productive hydrolysis of the nucleotide sugar in the absence of acceptor.

Sialyltransferases are characterized by folds composed primarily of α/β/α sandwiches, much like the Rossmann fold which contains a six-stranded parallel β-sheet having a 321456 topology. The GT-B fold, in particular, includes two separate Rossmann-like domains with a connecting linker region. The catalytic site is located between the domains. High structural conservation is known to exists between glycosyltransferases in the GT-B family, as described by Breton et al. (*Glycobiology,* 2006, 16(2): 29R-37R), which is incorporated herein by reference in its entirety.

In some embodiments, the native 2,6ST is a GT80 sialyltransferase. The GT80 family of enzymes includes prokaryotic α2,3-sialyltransferases, α2,6-sialyltransferases, and bifunctional α2,3/α2,6-sialyltransferases (see, e.g., Audry et al. *Glycobiology,* 2011, 21(6):716-726), classified under EC 2.4.99.4 and EC2.4.99.1. GT80 sialyltransferases exhibit a GT-B fold and include two short conserved motifs (D/E-D/E-G and H-P), as described by Freiberger et al. (*Mol. Microbiol.* 2007, 65:1258-1275). The D/E-D/E-G motif is believed to interact with the lactose acceptor and act as a general base in catalysis. The H-P motif is believed to be involved in CMP binding and stabilization of the phosphate leaving group.

In some embodiments, the 2,6ST variant includes a native sialyltransferase sequence (e.g., a native GT80 sialyltransferase sequence), normally expressed by a bacterial species, and one or more amino acid substitutions as described herein. For example, the native sialyltransferase may be expressed by a *Photobacterium* species, a *Vibrio* species, a *Pasteurella* species, an *Actinobacillus* species, an *Avibacterium* species, a *Bibersteinia* species, a *Citrobacter* species, a *Glaesserella* species, a *Haemophilus* species, a *Pasteurellaceae* species, or a *Shewanella* species.

In some embodiments, the native sialyltransferase is expressed by a *Photobacterium* species (e.g., *Photobacterium* damselae, *Photobacterium* sp. JT-ISH-224, *Photobacterium leiognathi*, or *Photobacterium phosphoreum*). Pd2,6ST from *P. damselae* (GenBank Accession No. BAA25316.1), for example, exhibits an N-terminal Rossmann-like domain and a C-terminal Rossmann-like domain. The N-terminal Rossmann-like domain (residues 112-334) contains a central seven-stranded parallel β-sheet (topology b9-b8-b7-b10-b11-b12-b13) sandwiched by seven α-helices on one side and four α-helices on the other side. The C-terminal Rossmann-like domain (residues 335-497) contains a central six-stranded parallel β-sheet (b16 b15 b14 b17 b18 b19) sandwiched by two α-helices on one side and five α-helices on the other side. The CMP-Neu5Ac substrate analog interacts more with the C-terminal Rossmann-like domain. Similar folds are exhibited by other sialyltransferases (e.g., other GT-B sialyltransferases including GT80 family sialyltransferases).

In some embodiments, the 2,6ST variant is a *P. damselae* Pd2,6ST variant comprising a polypeptide sequence corresponding to residues 112-334 of SEQ ID NO:1, or a catalytically active portion thereof, and one or more amino substitutions therein, the amino acid substitutions providing improved α2-6-specific sialidase activity as compared to wild-type Pd2,6ST. The amino acid substitutions may be made, for example, at residues 112-334 of SEQ ID NO: 1, or at residues at 335-497 of SEQ ID NO: 1. The amino acid substitutions may also be made within the analogous regions of other sialidases containing a GT-B fold including, but not limited to, GT80 sialyltransferases such as *Photobacterium* sp. JT-ISH-224 α-2,6 ST (SEQ ID NO:3), *P. multocida* PmST1 (SEQ ID NO:4), and *P. phosphoreum* JT-ISH-467 α-/β-galactoside α-2,3-ST (SEQ ID NO:5).

In some embodiments, the amino acid substitutions may be made in an α-helix flanking either side of β-sheet of the N-terminal Rossmann-like domain in the GT-B fold (e.g., within residues 232-240 of SEQ ID NO:1 or within the analogous regions of another sialyltransferases containing a GT-B fold). It is believed that amino acid substitutions in this region, e.g., an S232L mutation in Pd2,6ST, can promote CMP-sialic acid hydrolysis by nucleophilic water in the second step of the sialidase mechanism. In this sense, the engineered substitution can be thought of as breaking the mechanism by which the native enzyme deters the use of water as an acceptor substrate. In some embodiments, the amino acid substitutions may be made in the hydrophobic core of the C-terminal Rossmann domain (e.g., within residues 352-366 of SEQ ID NO:1 or within the analogous regions of another sialyltransferases containing a GT-B fold). This region is typically buried in the absence of substrates but opens upon substrate binding to expose residues (e.g., Trp361 of Pd2,6ST) that contact the sialic acid targeted for cleavage. In some embodiments, the 2,6ST variant includes one or more amino acid substitutions at residues corresponding to residues 232, 356, and 361 as determined with reference to SEQ ID NO: 1. In some embodiments, the amino acid substitutions are selected from the group consisting of S232L, T356S, and W361F.

In some embodiments, the 2,6ST variant is a *P. multocida* PmST1 variant comprising a polypeptide sequence corresponding to SEQ ID NO:4, or a catalytically active portion thereof, and amino acid substitutions at one or more of positions 34, 144, 265, and 270 as determined with reference to SEQ ID NO:4. In some embodiments, the PmST1 variant comprises one, two, three, or four substitutions selected from P34H, M144L, T265S, and W270F as determined with respect to SEQ ID NO:4.

Further examples of GT80 sialyltransferases that can be engineered to provide neosialidases according to the present disclosure include, but are not limited to, those set forth in Table 1. Other sialyltransferases, e.g., other GT-B sialyltransferases, can be engineered in a similar manner. Mutations can be introduced and improvements in sialidase activity can be screened using the blue-white assay as described herein or another screening method (e.g., by monitoring sialoside hydrolysis using a chromatographic technique such as reverse-phase HPLC).

In some embodiments, screening of 2,6ST variants, or other target sialidases can be conducted by:

(i) culturing a host cell under conditions sufficient to express a target sialidase in the host cell, wherein the host cell expresses β-galactosidase;

(ii) combining the cultured cells from step (i) with a screening compound according to Formula I (I)

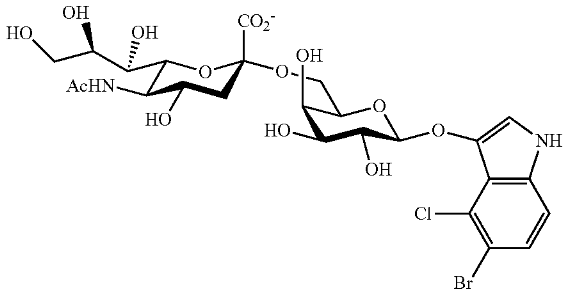

under conditions sufficient to form an indigo product in the presence of the target sialidase and the β-galactosidase; and (iii) detecting the sialidase activity in the host cell by detecting a blue color in the host cell due to formation of the indigo product.

In some embodiments the indigo product is a compound according to Formula Ia:

(Ia)

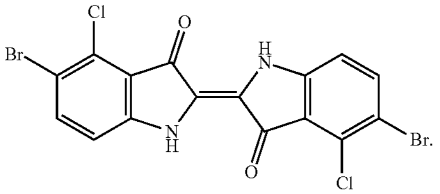

The screening compound of Formula I may be added directly to growth medium used for cell culture (e.g., an agar plate). Alternatively, sialidase activity can be assessed by transferring host cells (e.g., *E. coli* colonies) to a support material such as a filter paper or a nitrocellulose membrane and exposing the support material to the screening compound in a second step. Host cells can be lysed on the support material (e.g., by chloroform vapor) to promote contact of the screening compound with sialidase expressed in the cells, if necessary.

TABLE 1

Native GT80 α2,6 sialyltransferase for use as engineering templates.

| Protein Name(s) | Organism | GenBank Accession No. |
|---|---|---|
| ACEE_10230 | *Actinobacillus equuli* subsp. *equuli* 19392 | AIZ80121.1 |
| ASU1_08750 | *Actinobacillus suis* ATCC 33415 | AIJ32009.1 |
| ASU2_08685 | *Actinobacillus suis* H91-0380 | AFU19871.1 |
| SAMEA4504061_01832 | *Actinobacillus suis* NCTC12996 | SNV37863.1 |

TABLE 1-continued

Native GT80 α2,6 sialyltransferase for use as engineering templates.

| Protein Name(s) | Organism | GenBank Accession No. |
|---|---|---|
| F542_16230 | *Bibersteinia trehalosi* USDA-ARS-USMARC-188 | AHG82339.1 |
| F543_17920 | *Bibersteinia trehalosi* USDA-ARS-USMARC-189 | AHG84654.1 |
| F544_6130 | *Bibersteinia trehalosi* USDA-ARS-USMARC-190 | AHG85844.1 |
| CMP-Neu5Ac: α-2,3-sialyltransferase (BtST1) (WQG_5820) | *Bibersteinia trehalosi* USDA-ARS-USMARC-192 | AGH37861.1 |
| A6J81_12085 | *Citrobacter braakii* FDAARGOS_253 | ARC41398.1 |
| CES93_20815 | *Citrobacter freundii* 705SK3 | ASG45876.1 |
| AM363_07760 | *Citrobacter freundii* AR_0116 | AXZ46858.1 |
| BTW28_04900 | *Citrobacter freundii* BD | APR30363.1 |
| C2U38_04605 | *Citrobacter freundii* complex sp. CFNIH3 | AUV24994.1 |
| MC47_000060 | *Citrobacter freundii* FDAARGOS_61 | AUT93851.1 |
| CUC52_01295 | *Citrobacter freundii* HM38 | AYL74229.1 |
| BFQ28_23795 | *Citrobacter freundii* SL151 | AOI32687.1 |
| CUC48_01280 | *Citrobacter freundii* UMH16 | AYL55320.1 |
| AL515_05950 | *Citrobacter* sp. FDAARGOS_156 | AMH13422.1 |
| CJD39_00220 | *Glaesserella* sp. 15-184 | AUI65092.1 |
| CMP-Neu5Ac: LacMU α-2,3-sialyltransferase (HD0053) | [*Haemophilus*] *ducreyi* 35000HP | AAP95068.1 |
| RY60_00200 | [*Haemophilus*] *ducreyi* CLU1 | AKO30250.1 |
| RZ57_00205 | [*Haemophilus*] *ducreyi* CLU2 | AKO31684.1 |
| RZ58_00200 | [*Haemophilus*] *ducreyi* CLU3 | AKO33135.1 |
| RZ59_00200 | [*Haemophilus*] *ducreyi* CLU4 | AKO34585.1 |
| RZ60_00200 | [*Haemophilus*] *ducreyi* CLU5 | AKO43395.1 |
| CEP76_03325 | [*Haemophilus*] *ducreyi* FDAARGOS_297 | ASE06764.1 |
| A6041_06590 | [*Haemophilus*] *ducreyi* GHA1 | ANF68209.1 |
| A6042_04515 | [*Haemophilus*] *ducreyi* GHA2 | ANF69236.1 |
| A6043_00030 | [*Haemophilus*] *ducreyi* GHA3 | ANF69856.1 |
| A6044_00520 | [*Haemophilus*] *ducreyi* GHA5 | ANF71482.1 |
| A6045_00975 | [*Haemophilus*] *ducreyi* GHA8 | ANF73109.1 |
| A6046_03050 | [*Haemophilus*] *ducreyi* GHA9 | ANF75048.1 |
| RZ61_00210 | [*Haemophilus*] *ducreyi* GU1 | AKO36020.1 |
| RZ62_00200 | [*Haemophilus*] *ducreyi* GU2 | AKO37475.1 |
| RZ63_00195 | [*Haemophilus*] *ducreyi* GU3 | AKO39029.1 |
| RZ64_00200 | [*Haemophilus*] *ducreyi* GU4 | AKO40520.1 |
| RZ65_00200 | [*Haemophilus*] *ducreyi* GU5 | AKO41974.1 |
| RZ66_00200 | [*Haemophilus*] *ducreyi* GU6 | AKO44776.1 |
| RZ67_00200 | [*Haemophilus*] *ducreyi* GU7 | AKO46182.1 |
| RZ68_00200 | [*Haemophilus*] *ducreyi* GU8 | AKO47523.1 |
| RZ69_00200 | [*Haemophilus*] *ducreyi* GU9 | AKO48908.1 |
| A6036_06760 | [*Haemophilus*] *ducreyi* VAN1 | ANF60953.1 |
| A6037_03615 | [*Haemophilus*] *ducreyi* VAN2 | ANF61891.1 |
| A6038_01230 | [*Haemophilus*] *ducreyi* VAN3 | ANF62866.1 |
| A6039_08175 | [*Haemophilus*] *ducreyi* VAN4 | ANF65524.1 |
| A6040_04630 | [*Haemophilus*] *ducreyi* VAN5 | ANF66400.1 |
| CMP-Neu5Ac α-2,3-sialyltransferase (PdST) | *Pasteurella dagmatis* DSM 22969 | AFY98851.1 |
| SAMEA4362423_01162 | *Pasteurella dagmatis* NCTC11617 | SNV70041.1 |
| C4O90_05700 | *Pasteurella multocida* 12601 | AWW62063.1 |
| DIS05_05040 | *Pasteurella multocida* 14424 | AWW55876.1 |
| DB278_07745 | *Pasteurella multocida* 20N | AWB53424.1 |
| Pmu3358_05300 | *Pasteurella multocida* 3358 | AWW51862.1 |
| C4O87_05305 | *Pasteurella multocida* 3361 | AWW57905.1 |
| Pmu_11250 | *Pasteurella multocida* 36950 | AET16017.1 |
| CLD34_05665 | *Pasteurella multocida* 375-A/15 | ATC22736.1 |
| DID83_04990 | *Pasteurella multocida* 4407 | AWW53873.1 |
| pm9n_00980 | *Pasteurella multocida* 9N | AWB54224.1 |
| CMP-Neu5Ac: α-2,3/2,6-sialyltransferase 1/sialidase (St1) (PmST1) | *Pasteurella multocida* ATCC 15742/P-1059 | AAY89061.1 |
| DR93_1878 | *Pasteurella multocida* ATCC 43137 | AIN48372.1 |
| DYY64_01790 | *Pasteurella multocida* BS168 | AXO02977.1 |
| DYY63_01790 | *Pasteurella multocida* EB168 | AXO00761.1 |
| ATO47_01155 | *Pasteurella multocida* F | AUL52899.1 |

TABLE 1-continued

Native GT80 α2,6 sialyltransferase for use as engineering templates.

| Protein Name(s) | Organism | GenBank Accession No. |
|---|---|---|
| A6J55_09650 | *Pasteurella multocida* FDAARGOS_216 | ARB74443.1 |
| A6J57_07470 | *Pasteurella multocida* FDAARGOS_218 | ARB76073.1 |
| CO688_02705 | *Pasteurella multocida* FDAARGOS_384 | ATF74348.1 |
| CRN72_02995 | *Pasteurella multocida* FDAARGOS_385 | ATN16749.1 |
| SAMEA4521464_01078 | *Pasteurella multocida* NCTC10322 | SNV68002.1 |
| NCTC10382_01150 | *Pasteurella multocida* NCTC10382 | SQI49292.1 |
| I927_03095 | *Pasteurella multocida* OH1905 | AKD39852.1 |
| AZI96_04705 | *Pasteurella multocida* Pm-3 | AON58064.1 |
| DYY61_01790 | *Pasteurella multocida* PM8-1 | AXN98542.1 |
| BV212_10580 | *Pasteurella multocida* Razi 0002 | APW58499.1 |
| BMF22_06505 | *Pasteurella multocida* Razi_Pm0001 | APB79704.1 |
| BTV67_08445 | *Pasteurella multocida* subsp. *multocida* CIRMBP-0884 | ARA70542.1 |
| PMCN01_1044 | *Pasteurella multocida* subsp. *multocida* HB01 | ANJ90272.1 |
| AW43_05840 | *Pasteurella multocida* subsp. *multocida* PMTB2.1 | AMM81927.1 |
| AWY89_02150 | *Pasteurella multocida* subsp. *multocida* RCAD0259 | AXQ71824.1 |
| NT08PM_1144 | *Pasteurella multocida* subsp. *multocida* str. 3480 | AFI46264.1 |
| PMCN03_1055 | *Pasteurella multocida* subsp. *multocida* str. HB03 | AHE64510.1 |
| PMCN06_1112 | *Pasteurella multocida* subsp. *multocida* str. HN06 | AFF24354.1 |
| PMCN07_1052 | *Pasteurella multocida* subsp. *multocida* str. HN07 | APW55636.1 |
| CMP-Neu5Ac: [galactosyl oligosaccharide] α-2,3/6-sialyltransferase 1 (St1) (PmST1) (PM0188) | *Pasteurella multocida* subsp. *multocida* str. Pm70 | AAK02272.1 |
| BTV66_07205 | *Pasteurella multocida* subsp. *septica* CIRMBP-0873 | ARA89377.1 |
| DYY62_01785 | *Pasteurella multocida* TB168 | AXN94678.1 |
| A4201_07805 | *Pasteurella multocida* USDA-ARS-USMARC-59910 | AUK34763.1 |
| A4202_02995 | *Pasteurella multocida* USDA-ARS-USMARC-59962 | AUK51318.1 |
| A4203_07855 | *Pasteurella multocida* USDA-ARS-USMARC-60213 | AUK32720.1 |
| A4205_03270 | *Pasteurella multocida* USDA-ARS-USMARC-60215 | AUK27744.1 |
| A4206_07920 | *Pasteurella multocida* USDA-ARS-USMARC-60224 | AUK40997.1 |
| A4207_07475 | *Pasteurella multocida* USDA-ARS-USMARC-60248 | AUK47287.1 |
| A4208_07910 | *Pasteurella multocida* USDA-ARS-USMARC-60380 | AUK36887.1 |
| A4209_03270 | *Pasteurella multocida* USDA-ARS-USMARC-60381 | AUK55583.1 |
| A4210_10710 | *Pasteurella multocida* USDA-ARS-USMARC-60385 | AUK50169.1 |
| A4211_07935 | *Pasteurella multocida* USDA-ARS-USMARC-60494 | AUK26511.1 |
| A4212_08630 | *Pasteurella multocida* USDA-ARS-USMARC-60675 | AUK45249.1 |
| A4213_07900 | *Pasteurella multocida* USDA-ARS-USMARC-60712 | AUK43056.1 |
| A4214_07895 | *Pasteurella multocida* USDA-ARS-USMARC-60713 | AUK38934.1 |
| A4215_07920 | *Pasteurella multocida* USDA-ARS-USMARC-60714 | AUK58512.1 |
| A4216_03010 | *Pasteurella multocida* USDA-ARS-USMARC-60717 | AUK29794.1 |
| C4O88_05305 | *Pasteurellaceae bacterium* 12591 | AWW59956.1 |
| CMP-Neu5Ac: β-galactoside α-2,6-sialyltransferase (Bst) Pd2,6ST | *Photobacterium damselae* JT0160 | BAA25316.1 |

TABLE 1-continued

Native GT80 α2,6 sialyltransferase for use as engineering templates.

| Protein Name(s) | Organism | GenBank Accession No. |
|---|---|---|
| BST98_04300 | *Photobacterium damselae* Phdp Wu-1 | AWK81336.1 |
| α-2,6-sialyltransferase/ α-2,6-linkage-specific neuraminidase (Plst6) | *Photobacterium leiognathi* JT-SHIZ-119 | BAI49484.1 |
| CMP-Neu5Ac: β-galactoside α-2,6-sialyltransferase (Plst6) | *Photobacterium leiognathi* JT-SHIZ-145 | BAF91416.1 |
| CMP-Neu5Ac: a-/β-galactoside α-2,3-sialyltransferase | *Photobacterium phosphoreum* JT-ISH-467 | BAF63530.1 |
| CMP-Neu5Ac: a-/β-galactoside α-2,3-sialyltransferase (pst3-224) | *Photobacterium* sp. JT-ISH-224 | BAF92025.1 |
| CMP-Neu5Ac: β-galactoside α-2,6-sialyltransferase (pst6-224) (Psp2,6ST) | *Photobacterium* sp. JT-ISH-224 | BAF92026.1 |
| swp_5060 | *Shewanella piezotolerans* WP3 | ACJ31674.1 |
| CMP-Neu5Ac: a/β-galactoside α-2,3-sialyltransferase (2,3st) | *Vibrio* sp. JT-FAJ-16 | BAF91160.1 |

Various embodiments of the present disclosure provide 2,6ST variants which are at least 75%, at least 80%, at least 85%, at least 90%, at least 95%, or at least 99% identical to the enzymes disclosed herein. "Identical" and "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 75%, at least 80%, at least 85%, at least 90%, at least 95%, or at least 99% identical over a specified region), when compared and aligned for maximum correspondence over a comparison window, or designated region as measured using one of the following sequence comparison algorithms or by manual alignment and visual inspection. These definitions also refer to the complement of a nucleic acid test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

In certain embodiments, an enzyme variant will have at least about 80%, e.g., at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to any one of the amino acid sequences set forth herein. In some embodiments, for example, the 2,6ST variant comprises an amino acid sequence having at least 70% identity to residues 16-497 of SEQ ID NO:1, or a catalytically active portion thereof. In some embodiments, the 2,6ST variant comprises an amino acid sequence having at least 90% identity to residues 16-497 of SEQ ID NO:1, or a catalytically active portion thereof.

In a related aspect, the present disclosure provides nucleic acids encoding 2,6ST variants as described herein. The nucleic acids can be generated from a nucleic acid template encoding the wild-type 2,6ST, using any of a number of known recombinant DNA techniques. Accordingly, certain embodiments of the present disclosure provide an isolated nucleic acid comprising a polynucleotide sequence encoding an 2,6ST variant (including, but not limited to, a polypeptide as set forth in SEQ ID NOS:1-5, or catalytically active portions thereof, containing one or more amino acid substitutions as described herein).

Using a 2,6ST variant-encoding nucleic acid as described above, a variety of expression constructs and vectors can be made. Generally, expression vectors include transcriptional and translational regulatory nucleic acid regions operably linked to the nucleic acid encoding the mutant sialyltransferase. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. In addition, the vector may contain a Positive Retroregulatory Element (PRE) to enhance the half-life of the transcribed mRNA (see, Gelfand et al. U.S. Pat. No. 4,666,848). The transcriptional and translational regulatory nucleic acid regions will generally be appropriate to the host cell used to express the sialyltransferase. Numerous types of appropriate expression vectors and suitable regulatory sequences are known in the art for a variety of host cells. In general, the transcriptional and translational regulatory sequences may include, e.g., promoter sequences, ribosomal binding sites, transcriptional start and stop sequences, translational start and stop sequences, and enhancer or activator sequences. Typically, the regulatory sequences will include a promoter and/or transcriptional start and stop sequences. Vectors also typically include a polylinker region containing several restriction sites for insertion of foreign DNA. Heterologous sequences (e.g., a fusion tag such as a His tag) can be used to facilitate purification and, if desired, removed after purification. The construction of suitable vectors containing DNA encoding replication sequences, regulatory sequences, phenotypic selection genes, and the mutant sialyltransferase of interest are prepared using standard recombinant DNA procedures. Isolated plasmids, viral vectors, and DNA fragments are cleaved, tailored, and ligated together in a specific order to generate the desired vectors, as is well-known in the art (see, e.g., Sambrook et al., *Molecular Cloning: A Laboratory Manual* (Cold Spring Harbor Laboratory Press, New York, N.Y., 2nd ed. 1989)).

Accordingly, some embodiments of the present disclosure provide an expression cassette comprising a 2,6ST variant-encoding nucleic acid as described herein operably linked to a promoter. In some embodiments, a vector comprising a 2,6ST variant-encoding nucleic acid as described herein is provided. In certain embodiments, the expression vector contains a selectable marker gene to allow the selection of transformed host cells. Selection genes are well known in the art and will vary with the host cell used. Suitable selection genes can include, for example, genes coding for ampicillin and/or tetracycline resistance, which enables cells transformed with these vectors to grow in the presence of these antibiotics.

In some embodiments, a nucleic acid encoding a sialyltransferase variant is introduced into a cell, either alone or in combination with a vector. By "introduced into," it is meant that the nucleic acids enter the cells in a manner suitable for subsequent integration, amplification, and/or expression of the nucleic acid. The method of introduction is largely dictated by the targeted cell type. Exemplary methods include $CaPO_4$ precipitation, liposome fusion, LIPOFECTIN®, electroporation, heat shock, viral infection, and the like.

In some embodiments, prokaryotes are used as host cells for the initial cloning steps described herein. Other host cells include, but are not limited to, eukaryotic (e.g., mammalian, plant and insect cells), or prokaryotic (bacterial) cells. Exemplary host cells include, but are not limited to, *Escherichia coli, Saccharomyces cerevisiae, Pichia pastoris, Sf*9 insect cells, and CHO cells. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3110 (ATCC No. 27,325), *E. coli* K12 strain DG116 (ATCC No. 53,606), *E. coli* X1776 (ATCC No. 31,537), and *E. coli* B; and other strains of *E. coli*, such as HB101, JM101, NM522, NM538, and NM539. Many other species and genera of prokaryotes including bacilli such as *Bacillus subtilis*, other enterobacteriaceae such as *Salmonella typhimurium* or *Serratia marcesans*, and various *Pseudomonas* species can all be used as hosts. Prokaryotic host cells or other host cells with rigid cell walls are typically transformed using the calcium chloride method as described in Sambrook et al., supra. Alternatively, electroporation can be used for transformation of these cells. Prokaryote transformation techniques are set forth in, for example Dower, in *Genetic Engineering, Principles and Methods* 12:275-296 (Plenum Publishing Corp., 1990); Hanahan et al., *Meth. Enzymol.,* 204:63, 1991. Plasmids typically used for transformation of *E. coli* include pBR322, pUCI8, pUCI9, pUCI18, pUC119, and Bluescript M13, all of which are described in sections 1.12-1.20 of Sambrook et al., supra. However, many other suitable vectors are available as well.

Accordingly, some embodiments of the present disclosure provide a host cell comprising a 2,6ST variant-encoding nucleic acid, expression cassette, or vector, as described herein. In some embodiments, a 2,6ST variant is produced by culturing a host cell transformed with an expression vector containing a nucleic acid encoding the sialyltransferase, under the appropriate conditions to induce or cause expression of the sialyltransferase. Methods of culturing transformed host cells under conditions suitable for protein expression are well-known in the art (see, e.g., Sambrook et al., supra). Suitable host cells for production of the 2,6ST variants from lambda pL promoter-containing plasmid vectors include *E. coli* strain DG116 (ATCC No. 53606) (see U.S. Pat. No. 5,079,352 and Lawyer, F. C. et al., *PCR Methods and Applications* 2:275-87, 1993, which are both incorporated herein by reference). Suitable host cells for production of the 2,6ST variants from T7 promoter-containing plasmid vectors include *E. coli* strain BL21 (DE3) and related lysogens (see, e.g., U.S. Pat. No. 5,693,489). Following expression, a 2,6ST variant can be harvested and isolated. In some embodiments, a cell including a recombinant nucleic acid as described herein is provided. The cells can be prokaryotic or eukaryotic. The cells can be mammalian, plant, bacteria, or insect cells.

III. METHODS FOR PRODUCING DE-SIALYLATED PRODUCTS

The 2,6ST variants provided herein can be used for the selective removal of N-acetylneuraminic acid (Neu5Ac) and other sialic acids from sialylated glycosides (also referred to as herein sialosides). For example, Pd2,6ST-S232L/T356S/W361F can selectively catalyze the removal of α2,6-linked Neu5Ac moieties from egg yolk sialoglycopeptide and other peptides and proteins bearing sialylated N-linked glycans.

Accordingly, another aspect of the present disclosure provides a method of producing a de-sialylated product. The method includes forming a reaction mixture containing a sialoside and a 2,6ST variant as described herein, under conditions sufficient to remove one or more sialic acid moieties from the sialoside. In some embodiments, the reaction mixture further comprises cytidine monophosphate (CMP) and/or magnesium chloride ($MgCl_2$). A number of suitable sialosides can be used in the methods provided herein. In some embodiments, the sialoside is a compound according to Formula II:

(II)

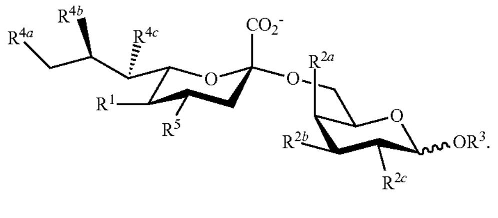

In sialosides of Formula II, $R^1$ is selected from —OH, —NHAc (i.e., —NHC(O)$CH_3$), and —NHGc (i.e., —NHC(O)$CH_2OH$). $R^{2a}$, $R^{2b}$, and $R^{2c}$ are independently selected from the group consisting of H, —OH, —OAc, and —NHAc. In some embodiments, $R^{2a}$ is —OH. In some embodiments, $R^{2a}$ and $R^{2b}$ are —OH. In some embodiments, $R^{2a}$, $R^{2b}$, and $R^{2c}$ are —OH. In some embodiments, $R^{2a}$ and $R^{2b}$ are —OH and $R^{2c}$ is —NHAc. $R^3$ can be a monosaccharide, an oligosaccharide, a polysaccharide, an amino acid, an oligopeptide, a polypeptide, a glycopeptide, a glyoprotein, a lipid, a glycolipid, or a natural product. Other $R^3$ groups, e.g., fluorophore-containing $R^3$ groups, can also be present in the acceptor glycosides. $R^{4a}$, $R^{4b}$, $R^{4c}$, and $R^5$ are independently selected from the group consisting of H, —OH, —$OCH_3$, —OAc, —NHAc, —$N_3$, and —$NH_2$. In some embodiments, $R^{4a}$, $R^{4b}$, $R^{4c}$, and $R^5$ are —OH.

In some embodiments, the sialoside is a compound according to Formula IIa:

(IIa)

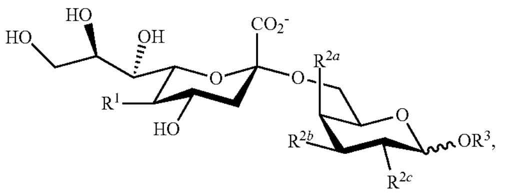

wherein $R^1$, $R^{2a}$, $R^{2b}$, $R^{2c}$ and $R^3$ have the definitions described above.

The methods provided herein include the formation of reaction mixtures that contain 2,6ST variants as described above. The 2,6ST variants can be, for example, isolated or otherwise purified prior to addition to the reaction mixture. As used herein, a "purified" enzyme refers to an enzyme which is provided as a purified protein composition wherein the enzyme constitutes at least about 50% of the total protein in the purified protein composition. For example, the enzyme (e.g., a 2,6ST variant) can constitute about 50%, 60%, 70%, 75%, 80%, 85%, 90%, 95%, or 99% of the total protein in the purified protein composition. In some embodiments, the 2,6ST variant in the reaction mixture is provided as a purified protein composition wherein the 2,6ST variant constitutes at least about 95% of the total protein in purified protein composition. The amount of the 2,6ST variant in a purified protein composition can be determined by any number of known methods including, for example, by polyacrylamide gel electrophoresis (e.g., SDS-PAGE) followed by detection with a staining reagent (e.g., Coomassie Brilliant Blue G-250, a silver nitrate stain, and/or a reagent containing a Psp26ST antibody). The 2,6ST variants and other enzymes used in the methods can also be secreted by a cell present in the reaction mixture. Alternatively, a 2,6ST variant or another enzyme can catalyze the reaction within a cell expressing the variant.

Reaction mixtures can contain additional reagents for use in glycosylation biochemical methods. For example, in certain embodiments, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, tetrahydrofuran, acetone, and acetic acid), salts (e.g., NaCl, KCl, $CaCl_2$, and salts of $Mn^{2+}$ and $Mg^{2+}$), detergents/surfactants (e.g., a non-ionic surfactant such as N,N-bis[3-(D-gluconamido)propyl]cholamide, polyoxyethylene (20) cetyl ether, dimethyldecylphosphine oxide, branched octylphenoxy poly(ethyleneoxy)ethanol, a polyoxyethylene-polyoxypropylene block copolymer, t-octylphenoxypolyethoxyethanol, polyoxyethylene (20) sorbitan monooleate, and the like; an anionic surfactant such as sodium cholate, N-lauroylsarcosine, sodium dodecyl sulfate, and the like; a cationic surfactant such as hexdecyltrimethyl ammonium bromide, trimethyl(tetradecyl) ammonium bromide, and the like; or a zwitterionic surfactant such as an amidosulfobetaine, 3-[(3-cholamidopropyl)dimethyl-ammonio]-1-propanesulfonate, and the like), chelators (e.g., ethylene glycol-bis(2-aminoethylether)-N,N,N',N'-tetraacetic acid (EGTA), 2-({2-[Bis(carboxymethyl)amino]ethyl} (carboxymethyl)amino)acetic acid (EDTA), and 1,2-bis(o-aminophenoxy)ethane-N,N,N',N'-tetraacetic acid (BAPTA)), reducing agents (e.g., dithiothreitol (DTT), β-mercaptoethanol (BME), and tris(2-carboxyethyl)phosphine (TCEP)), and labels (e.g., fluorophores, radiolabels, and spin labels).

Buffers, cosolvents, salts, detergents/surfactants, chelators, reducing agents, and labels can be used at any suitable concentration, which can be readily determined by one of skill in the art. In general, buffers, cosolvents, salts, detergents/surfactants, chelators, reducing agents, and labels are included in reaction mixtures at concentrations ranging from about 1 μM to about 1 M. For example, a buffer, a cosolvent, a salt, a detergent/surfactant, a chelator, a reducing agent, or a label can be included in a reaction mixture at a concentration of about 1 μM, or about 10 μM, or about 100 μM, or about 1 mM, or about 10 mM, or about 25 mM, or about 50 mM, or about 100 mM, or about 250 mM, or about 500 mM, or about 1 M. In some embodiments, the reaction mixtures contain a sialoside (e.g., 0.1 μM-5 mM sialoside), a 2,6ST variant (e.g., 0.1-10 μM enzyme), and one or more components selected from a buffer, a cosolvent, a salt, a detergent/surfactant, a chelator, and a reducing agent. In some embodiments, the reaction mixture further includes magnesium chloride (e.g., 5-25 mM $MgCl_2$) and/or a nucleotide sugar such as cytidine monophosphate (e.g., 0.1-5 mM CMP). In some embodiments, the reaction mixtures consist essentially of a sialoside, a 2,6ST variant as described herein, and one or more components selected from a buffer, a cosolvent, a salt, a detergent/surfactant, a chelator, and a reducing agent. In some embodiments, the reaction mixtures consist essentially of a sialoside, a nucleotide sugar, a 2,6ST variant as described herein, and one or more components selected from a buffer, a cosolvent, a salt, a detergent/surfactant, a chelator, and a reducing agent.

Reactions are conducted under conditions sufficient to remove one or more sialic acid moieties from the sialoside. The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 4.5 to about 10. The reactions can be conducted, for example, at a pH of from about 5 to about 9. In some embodiments, the reaction is conducted at a pH around 6.0. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. Other reaction conditions may be employed in the methods, depending on the identity of a particular 2,6ST variant or sialoside.

The sialosides use in the methods can include a variety of sialylated oligosaccharides, sialylated polysaccharides, sialylated glycopeptides, sialylated glycoproteins, sialylated glycolipids, and sialylated natural products. Examples of sialylated natural products include, but are not limited to, non-ribosomal glycopeptides (such as bleomycin), glycoalkaloids (such as solanine), ginsenosides (such as sanchinoside C1), aminoglycosides (such as gentamicin, kanamycin, neomycin, and streptomycin), avermectins, and anthracyclines (such as daunorubicin). Examples of sialylated glycolipids include, but are not limited to, glyceroglycolipids (such as monogalactosyldiacylglycerols, digalactosyldiacylglycerols, and sulfoquinovosyl diacylglycerols), glycerosphingolipids (such as cerebrosides, gangliosides, and globosides), and glycophosphatidylinositols (e.g., 1-phosphatidyl-L-myo-inositol 2,6-di-O-α-D-mannopyranoside). Examples of sialylated glycoproteins include, but are not limited to, mucins, immunoglobulins, lectins, and collagens.

Advantageously, a target sialoside can be conveniently prepared by using the sialyltransferase activity of the native 2,6ST, by itself or in conjunction with other enzymes in a one-pot multi-enzyme synthesis, for subsequent use in screening steps during engineering of the same 2,6ST to improve neosialidase activity. Preparation of the target sialosides using sialyltransferases and other enzymes (e.g., CMP-sialic acid synthetases, sialic acid aldolases, kinases, dehydrogenases, nucleotide sugar pyrophosphorylases, and/or pyrophosphatases) can be conducted according to procedures such as those described in U.S. Pat. No. 9,938,510 and US 2016/0177275, which are incorporated herein by reference in their entirety.

IV. EXAMPLES

Example 1. One-Pot Two-Enzyme Synthesis of Neu5Acα2-6GalβX (1) for Sialidase Activity Screening Chemicals were purchased and used as received. NMR spectra were recorded in the NMR facility of the University of California, Davis, on a Bruker Avance-800 NMR spectrometer (800 MHz for $^{1}H$, 200 MHz for $^{13}C$). Chemical shifts are reported in parts per million (ppm) on the δ scale. High resolution (HR) electrospray ionization (ESI) mass spectra were obtained using a Thermo Electron LTQ-Orbitrap Hybrid MS at the Mass Spectrometry Facility in the University of California, Davis. N-Acetylneuraminic acid (Neu5Ac) was from Inalco (Italy). Cytosine 5'-triphosphate (CTP) was purchased from Hangzhou Meiya Pharmaceutical Co. Ltd. X-Gal was purchased from Sigma. Neu5Acα2-6GalβpNP (2), Neu5Acα2-3GalβpNP (3), Kdnα2-6GalβpNP (5), Neu5Gcα2-6GalβpNP (6), and Neu5Acα2-6GalNAcβpNP (7), Neu5Acα2-8Neu5Acα2-3GalβpNP (4), and Neu5Acα2-6LacβMU were synthesized as described previously. See, Chokhawala, Chen, et al. *Chembiochem* 2007, 8, 194-201; Tasnima, Chen, et al. *Org. Biomol. Chem.* 2016, 15, 160-167; and Cheng, Chen, et al. *Glycobiology* 2010, 20, 260-268; which references are incorporated herein by reference in their entirety.

A reaction mixture in a total volume of 20 mL containing Tris-HCl buffer (100 mM, pH 8.5), 5-bromo-4-chloro-3-indolyl-β-D-galactopyranosides (X-Gal, 50 mg, 0.122 mmol), Neu5Ac (57 mg, 0.184 mmol), CTP (97 mg, 0.184 mmol), DMF (7%), $MgCl_2$ (20 mM), NmCSS (2.5 mg), and Psp2,6ST (4.0 mg) were incubated in a shaker at 30° C. for 18 h. The reaction was stopped by adding 20 mL of 95% ethanol followed by incubation at 4° C. for 30 minutes. After centrifugation, the supernatant was concentrated and purified using a C18 column on a CombiFlash Rf 200i system eluted with a gradient of 0-100% acetonitrile in water for 20 minutes and a 30 mL $min^{-1}$ flow rate. The collection fraction containing the desired product was collected and dried to give Neu5Acα2-6GalβX as a white powder (81 mg, 92%). $^{1}H$ NMR (800 MHz, MeOD) δ 7.18 (d, J=8.8 Hz, 1H), 7.14 (bs, 1H), 7.04 (d, J=8.8 Hz, 1H), 4.58 (d, J=8.0 Hz, 1H), 3.93-3.40 (m, 11H), 2.77 (d, J=12.8 and 4.8 Hz, 1H), 1.92 (s, 3H), 1.53 (t, J=12.0 Hz, 1H); $^{13}C$ NMR (200 MHz, MeOD) δ 173.96, 173.13, 136.65, 133.36, 125.39, 123.78, 117.98, 113.36, 111.81, 111.11, 104.08, 100.40, 73.96, 73.37, 72.93, 71.52, 71.17, 68.84, 68.49, 68.08, 62.98, 62.42, 52.66, 41.18, 21.14. HRMS (ESI) m/z calcd for $C_{25}H_{31}BrClN_2O_{14}$ $[M-H]^-$ 697.0653, found 697.0609.

Example 2. Preparation of Enzyme Variant Library

Mutagenesis.

Pd2,6ST libraries were constructed using either the Q5 Mutagenesis Kit (D229X and W361X) or the QuikChange II Site Directed Mutagenesis kit using the primers set forth in Table 2

TABLE 2

| Primer | SEQ ID NO | Sequence |
|---|---|---|
| D229X_f | SEQ ID NO: 6 | 5'-NNKGGTTCTTCTGAATATGTAAGTTTATATCAATGG-3' |
| D229X_r | SEQ ID NO: 7 | 5'-ATCATACAAACTAATATGAGAAATTTTCACCTTCT CG-3' |
| S232X_f | SEQ ID NO: 8 | 5'-AATTTCTCATATTAGTTTGTATGATGATGGTTCTNN KGAATATGTAAGTTTATATCAATGGAAAGATACAC-3' |
| S232X_r | SEQ ID NO: 9 | 5'-GTGTATCTTTCCATTGATATAAACTTACATATTCM NNAGAACCATCATCATACAAACTAATATGAGAAATT-3' |
| T356X_f | SEQ ID NO: 10 | 5'-ACAATATTCACAATCCCCACTACCAAACTTTATTTT TNNKGGCACAACAACTTTTGCTG-3' |
| T356X_r | SEQ ID NO: 11 | 5'-CAGCAAAAGTTGTTGTGCCMNNAAAAATAAAGTT TGGTAGTGGGGATTGTGAATATTGT-3' |

TABLE 2-continued

| Primer | SEQ ID NO | Sequence |
|---|---|---|
| W361X_f | SEQ ID NO: 12 | 5'-NNKGCTGGGGGGGAAACG-3' |
| W361X_r | SEQ ID NO: 13 | 5'-AGTTGTTGTGCCGGTAAAAATAAAGTTTGG-3' |
| A403X_f | SEQ ID NO: 14 | 5'-GACTACGATCTATTTTTCAAGGGGCATCCTNNKGG TGGCGTTATTAACG-3' |
| A403X_r | SEQ ID NO: 15 | 5'-CGTTAATAACGCCACCMNNAGGATGCCCCTTGAA AAATAGATCGTAGTC-3' |
| I425X_f | SEQ ID NO: 16 | 5'-TGATATGATCAATATTCCAGCCAAGNNKTCATTTG AGGTCTTGATGATGACGG-3' |
| I425X_r | SEQ ID NO: 17 | 5'-CCGTCATCATCAAGACCTCAAATGAMNNCTTGGCT GGAATATTGATCATATCA-3' |

The assembled DNA was transformed into *E. coli* 10 G electrocompetent cells (Lucigen). Ten percent of the transformed cells were plated on LB agar plates supplemented with ampicillin in order to determine the number of total transformants. The remaining transformed cells were diluted into fresh LB media (10 g $L^{-1}$ tryptone, 5 g $L^{-1}$ yeast extract, and 10 g $L^{-1}$ NaCl) supplemented with ampicillin, grown overnight at 37° C. 250 rpm, and the plasmid DNA was isolated. This DNA was transformed into homemade chemically competent *E. coli* BL21(DE3) cells.

Example 3. Sialidase Activity Screening

Library Screening.

Mutant libraries were transformed to BL21(DE3) chemically competent cells and plated on LB-agar plates supplemented with ampicillin. Following overnight incubation at 37° C., colonies were lifted onto 0.45 μm 47 mm Mixed Cellulose Esters Surfactant-Free Membrane Filters (Millipore). These nitrocellulose filters were carefully placed colony-side up on LB-agar plates supplemented with ampicillin and 0.1 mM IPTG, and these plates were incubated for 3 hours at 37° C. Meanwhile, the original LB-agar plates were incubated for 3-5 hours at 37° C. until the colonies regrew and then stored at 4° C. as master plates. The filters were then suspended over chloroform vapors for 10 minutes, briefly air dried, and were placed colony-side up on 55 mm Whatman filter paper soaked with 0.5 mL of the assay solution. For the first two rounds, the assay solution contained 3 mM Neu5Acα2-6GalβX, 0.5 mM CMP, 100 mM MES pH 5.5, and $MgCl_2$ (10 mM). For the third and fourth rounds, the assay solution contained Neu5Acα2-6GalβX (3 mM), Tris-HCl (pH 7.0, 100 mM), and $MgCl_2$ (10 mM). Reactions were conducted at 37° C. with regular examination of the filters for the development of blue color.

To allow easy identification of mutants with improved α2-6-sialidase activity, a novel blue-white membrane-blot high-throughput screening method was developed. To do this, an X-Gal-like α2-6-sialoside probe Neu5Acα2-6GalβX (1) (FIG. 1) was designed and synthesized. The screening works similarly to a plate-based high-throughput method for linkage-specific sialidase substrate specificity studies using para-nitrophenyl sialyl galactosides (Siaα2-3/6/8GalβpNP). Enzymatic cleavage of the α2-6-linked sialic acid on the Neu5Acα2-6GalβX probe by active Pd2,6ST mutants expressed in *E. coli* BL21(DE3) cells forms 5-bromo-4-chloro-3-indolyl-D-galactopyranoside (GalβX or X-Gal). The terminal galactose (Gal) residue is then rapidly hydrolyzed by endogenous β-galactosidase to yield the indole aglycone. This aglycone spontaneously dimerizes and forms a bright blue precipitate (FIG. 1). To avoid potential problems with membrane impermeability of the probe and minimize the amount of the probe used, colonies are not screened directly on agar plates but are instead lifted onto nitrocellulose filters, induced to express the mutant proteins, lysed over chloroform vapors, and screened by soaking the nitrocellulose filter in the Neu5Acα2-6GalβX solution.

The ease and high throughput of this assay allowed mutant libraries to be screened as quickly as they could be generated. Therefore, each round of mutagenesis ended upon identification of an improved variant, and further mutagenesis was performed on the improved variant to provide libraries for the next round of saturation mutagenesis.

Figure 2:
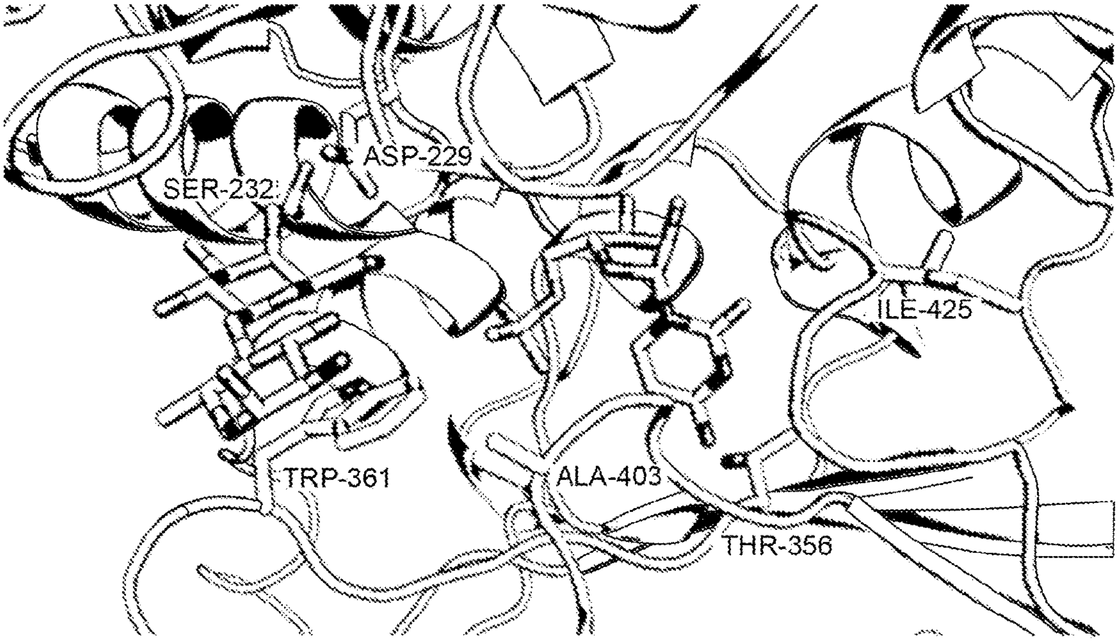
FIG. 2 shows the substrate binding site of Δ15Pd2,6ST(N) structure based on the co-crystal structure of Δ16Psp2,6ST (PDB ID: 2Z4T) with CMP and lactose. Structural modelling was performed with SWISS-MODEL.

Considerable structural information is available for GT80 sialyltransferases, including the binary complex structure (PDB ID: 4R84) of Δ15Pd2,6ST(N) with CMP-3F(a)Neu5Ac, the ternary complex structure (PDB ID: 2Z4T) of *Vibrionaceae photobacterium* sp. JT-ISH-224 α2-6-sialyltransferase (or Δ16Psp2,6ST) with cytidine 5'-monophosphate (CMP) and acceptor lactose, and the ternary complex structure (PDB ID: 2IHZ) of *Pasteurella multocida* sialyltransferase 1 (Δ24PmST1) with donor analogue CMP-3F(a)Neu5Ac and lactose. Analysis of these structures identified four (D229, 5232, W361, and A403) of the six residues ultimately chosen for mutagenesis (FIG. 2). T356 and 1425 were also chosen based on previously described mutants of PmST1 and Pd2,6ST, respectively, with increased sialyltransferase activity.

Figure 3:
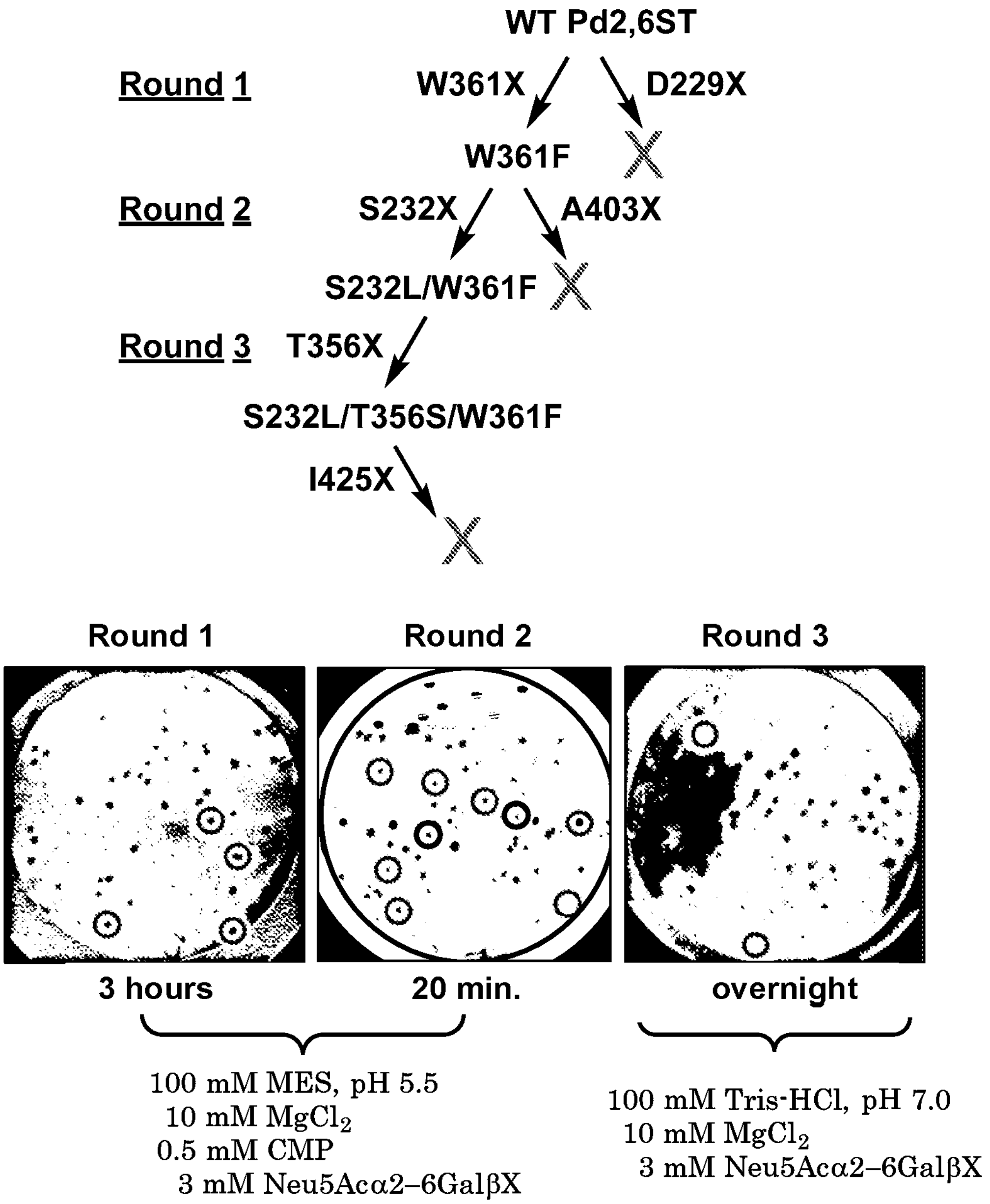
FIG. 3 shows the sequential saturation mutagenesis and blue/white colony screening of Pd2,6ST mutants for enhanced α2-6-sialidase activity

The first two residues targeted for mutagenesis were D229, the catalytic aspartate, and W361, a tryptophan sitting underneath the lactose and hydrogen bonded to the 7-OH of CMP-3F(a)Neu5Ac in PmST1 structure 2IHZ. Mutating D229 was a test of the proposed mechanism, as any detectable sialidase activity from mutants at this position would be evidence that the proposed catalytic function of D229 was incorrect. No improved variants were found from this library. In comparison, several colonies from the W361X library became noticeably blue after approximately 2 hours (FIG. 3). All of these colonies were found to have the same W361F amino acid mutation.

From the W361F mutant, libraries S232X and Δ403X were generated. Mutations of S232 and the homologous residue in related enzymes have been shown to affect a wide variety of properties including donor hydrolysis and sialidase activities, donor specificity, and acceptor specificity. Δ403 aligns with PmST1 residue R313, which has been found to affect sialidase activity. From the Δ403X library, the colonies that turned blue first were those retaining Δ403. However, in the S232X library, several colonies turned noticeably blue after only 20 minutes (FIG. 3). These colonies were sequenced and all were found to have the S232L mutation.

From the S232L/W361F mutant, the next library screened was T356X. Mutations at this site were previously found to improve the sialyltransferase activity of PmST1. Interestingly, this site is positioned near the nucleotide binding region of the active site and does not interact with any part of the sialoside. This library was screened at pH 7.0 and with no supplemented CMP in order to slow the reaction down and improve visual detection of the fastest color development. Two colonies turned light blue with overnight incubation and were found to encode the T356S mutation (FIG. 3). From the S232L/T356S/W361F mutant, the I425X library was generated. This site was found to also improve sialyltransferase activity of Pd2,6ST in the same work that identified the importance of T356. However, no improved α2-6-neosialidase variants were found from this library.

Using the Pd2,6ST S232L/T356S/W361F triple mutant with overall improved α2-6-neosialidase activity, CMP-Neu5Ac produced as an intermediate during the cleavage of Neu5Acα2-6LacβMU was detected by high resolution mass spectrometry. This provided additional evidence for the two-step, reverse sialylation followed by CMP-sialic acid hydrolysis process proposed for the sialidase activity of GT80 family multifunctional sialyltransferases.

The blue/white screening method used for the neosialidase engineering can be easily modified for the engineering of other neoglycosidases using suitable X-based probes. The throughput and simplicity of this method makes the engineering of neoglycosidases practical for non-specialists without expensive equipment such as automated liquid handling systems and microplate reader spectrophotometers. It is particularly convenient that the disaccharide-X probes can be synthesized from commercially available monosaccharide-X building blocks using the engineering target's wild-type glycosyltransferase activity.

Example 4. Study of Neosialidase Properties

Overexpression and Purification.

Flasks containing 1 L of autoclaved LB media supplemented with ampicillin (100 μg $mL^{-1}$) were inoculated with 1 mL of overnight cultured *E. coli* BL21(DE3) cells harboring the mutant plasmids. The 1 L cultures were grown at 37° C. until $OD_{600\ nm}$ reached 0.6 to 1.0, then expression was induced with isopropyl β-D-1-thiogalactoside (IPTG) to a final concentration of 0.1 mM and the cells shaken at 20° C. overnight. Cells were harvested in a Sorvall Legend RT centrifuge at 4000 rpm for 30 minutes, resuspended in 20 mL of Tris-HCl (pH 7.5, 100 mM) and lysed by sonication with the following method: amplitude at 65%, 10 s pulse on and 20 s pulse off for 18 cycles. The lysate was collected after centrifugation at 8000 pm for 30 minutes and then loaded onto a $Ni^{2+}$-NTA affinity column at 4° C. that was pre-equilibrated with 6 column volumes of binding buffer (50 mM Tris-HCl buffer, pH 7.5, 10 mM imidazole, 0.5 M NaCl). The column was washed with 10 column volumes of binding buffer and 10 column volumes of washing buffer (50 mM of Tris-HCl buffer, pH 7.5, 50 mM of imidazole, 0.5 M of NaCl) sequentially to wash away the nonspecific binding protein. The target protein was eluted using Tris-HCl buffer (50 mM, pH 7.5) containing 200 mM of imidazole and 0.5 M NaCl. Fractions containing the purified protein were combined and dialyzed against Tris-HCl buffer (20 mM, pH 7.5) supplemented with 10% glycerol. The enzyme solutions were aliquoted, flash frozen in liquid $N_2$, and stored at −20° C.

pH Profile.

Reactions were performed in duplicate at 37° C. for 30 minutes with a suitable buffer (100 mM MES from pH 4 to 6 or 100 mM Tris-HCl from pH 6.5 to 8.5), $MgCl_2$ (10 mM), Neu5Acα2-6LacβMU (1 mM), and CMP (0.5 mM). Reactions were stopped by adding an equal volume of pre-chilled methanol. The mixtures were incubated on ice for 30 minutes and centrifuged at 13,000 rpm for 5 minutes. Supernatants were analyzed with an Infinity 1290-II HPLC equipped with a UV-Vis detector (Agilent Technologies, CA). The HPLC procedure utilized a ZORBAX Eclipse Plus C18 Rapid Resolution HD 1.8 μm particle 2.1×50 mm column (Agilent Technologies, CA), an isocratic flow of 1 mL $min^{-1}$ for a 9% acetonitrile and 91% aqueous solution containing 0.1% TFA, and an injection volume of 2 μL. The 4-methylumbelliferone absorbance signal was monitored at 315 nm.

Neosialidase Kinetics.

Reactions were performed in duplicate at 37° C. for 10 to 30 minutes with Tris-HCl (100 mM, pH 6.0), $MgCl_2$ (10 mM), CMP (0.5 mM), enzyme (7.0 μM Pd2,6ST W361F, 0.32 μM Pd2,6ST S232L/W361F, 0.070 μM Pd2,6ST S232L/T356S/W361F), and varying concentrations (0.5, 1.0, 2.0, and 5.0 mM) of Neu5Acα2-6LacβMU. Reactions were stopped by adding an equal volume of pre-chilled methanol. The mixtures were incubated on ice for 30 minutes and centrifuged at 13,000 rpm for 5 minutes. Supernatants were analyzed with a P/ACE™ MDQ capillary electrophoresis (CE) system equipped with a UV-Vis detector (Beckman Coulter, Fullerton, Calif.). The CE procedure utilized a 75 μm i.d. capillary, 25 KV/80μÅ, 5 s vacuum injections, was monitored at 315 nm, and used sodium tetraborate (25 mM, pH 9.4) buffer as the running buffer. The apparent kinetic parameters were obtained by fitting the experimental data from duplicate assays into the Michaelis-Menten equation using Grafit 5.0.

Donor Hydrolysis Kinetics.

Reactions were performed in duplicate at 37° C. for 10 to 30 minutes with Tris-HCl (100 mM, pH 8.5), $MgCl_2$ (10 mM), enzyme (0.030 μM Pd2,6ST S232L/T356S/W361F), and varying concentrations (2.0, 5.0, 10.0, and 20.0 mM) of CMP-Neu5Ac. Reactions were stopped by adding an equal volume of pre-chilled methanol. The mixtures were incubated on ice for 30 minutes and centrifuged at 13,000 rpm for 5 minutes. Supernatants were analyzed with a P/ACE MDQ capillary electrophoresis (CE) system equipped with a UV-Vis detector (Beckman Coulter, Fullerton, Calif.). The CE procedure utilized a 75 μm i.d. capillary, 25 KV/80μÅ, 5 s vacuum injections, was monitored at 254 nm, and used sodium tetraborate (25 mM, pH 9.4) buffer as the running buffer. The apparent kinetic parameters were obtained by fitting the experimental data from duplicate assays into the Michaelis-Menten equation using Grafit 5.0.

Linkage Specificity Assays.

Reactions were performed in duplicate at 37° C. for 30 minutes in MES buffer (100 mM, pH 6.0), $MgCl_2$ (10 mM), CMP (0.5 mM), and 1 mM substrate. Enzyme concentrations were 0.030 μM for 2, 0.30 μM for 7, 3.0 μM 6, and 30.0 μM for 3-5. These conditions provided testing at initial rates (1.2-24% yield) for each substrate. Reactions were stopped by adding an equal volume of pre-chilled methanol. The mixtures were incubated on ice for 30 minutes and centrifuged at 13,000 rpm for 5 minutes. Supernatants were analyzed with an Infinity 1290-II HPLC equipped with a UV-Vis detector (Agilent Technologies, CA). The HPLC procedure utilized a ZORBAX Eclipse Plus C18 Rapid Resolution HD 1.8 μm particle 2.1×50 mm column (Agilent Technologies, CA), an isocratic flow of 1 mL min' for a 9% acetonitrile and 91% aqueous solution containing 0.1% TFA, and an injection volume of 2 μL. The para-nitrophenyl absorbance signal was monitored at 315 nm.

Figure 4:
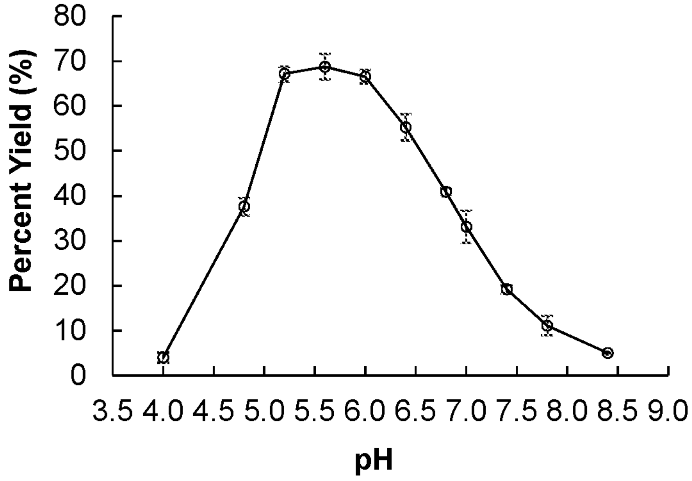
FIG. 4 shows the pH-profile of Pd2,6ST S232L/T356S/W361F neosialidase.

The pH profile study of the neosialidase activity of the Pd2,6ST S232L/T356S/W361F mutant was carried out using Neu5Acα2-6LacβMU as the substrate (FIG. 4). The optimal pH was found to be between 5.2 and 6.0. This agreed with previous pH profiles of sialyltransferase-catalyzed sialidase activity, suggesting that the engineering process did not significantly alter the optimal pH.

Three Pd2,6ST mutants including W361F, S232L/W361F, and S232L/T356S/W361F were kinetically characterized for neosialidase activity using Neu5Acα2-6LacβMU as the substrate (Table 3). The use of this probe with a different aglycone was a precaution to avoid mistaking improved recognition of the indole in 1 for improved neosialidase activity. Gratifyingly, the Pd2,6ST S232L/T356S/W361F triple mutant displayed 101-fold improved α2-6-sialidase activity compared to the wild-type enzyme. Relative to the activity of human NEU2 (hNEU2), an α2-3/6/8-sialidase, the Pd2,6ST S232L/T356S/W361F neosialidase displayed nearly 22-fold higher activity on a similar Neu5Acα2-6-containing probe. The high activity of the Pd2,6ST triple mutant was derived almost entirely through an increase in $k_{cat}$. However, the kinetic constants for the intermediate mutants show that each mutation had a greatly different effect on $k_{cat}$ and $K_M$. The W361F mutation resulted in a 2.35-fold increase in sialidase activity via a decrease in $k_{cat}$ but a larger decrease in $K_M$. Addition of the S232L mutation had little effect on $K_M$ but greatly enhanced $k_{cat}$ and provided the largest single-round gain in activity. The additional T356S mutation provided another large gain for $k_{cat}$ but also increased the $K_M$ nearly to that of the wild-type enzyme. The donor hydrolysis activity of the triple mutant was found to have increased 337-fold from the wild-type (Table 4).

Figure 5:
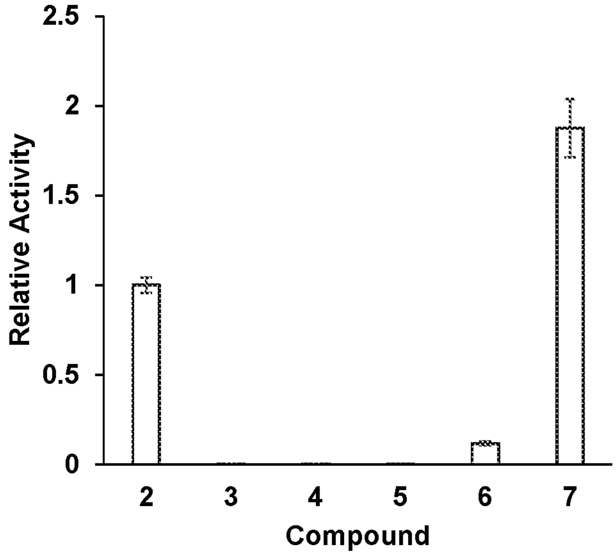
FIG. 5 shows the relative activities of Pd2,6ST S232L/T356S/W361F toward sialosides (2-7) with various sialic acid forms and linkages. Error bars represent standard deviations from duplicated assay results.
Figure 5:
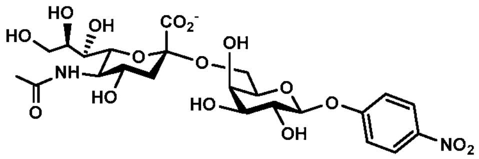
Figure 5:
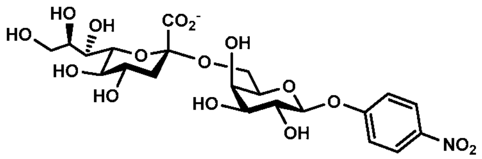
Figure 5:
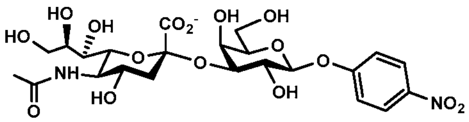
Figure 5:
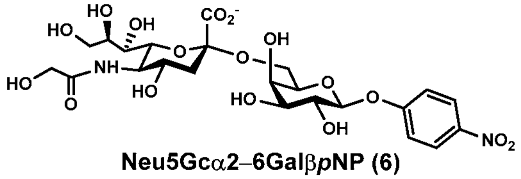
Figure 5:
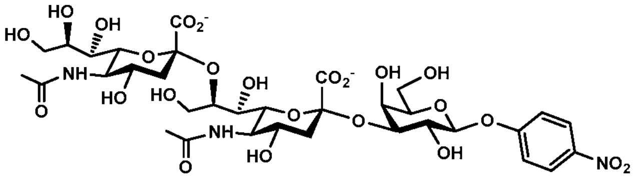
Figure 5:
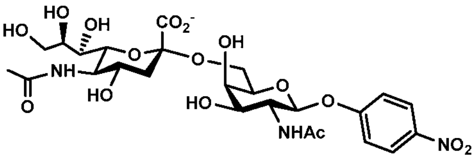

The substrate specificity of the Pd2,6ST S232L/T356S/W361F triple mutant was investigated by high-performance liquid chromatography (HPLC) analysis using probes containing varied linkages (α2-3/6/8), different sialic acid forms including NeuSAc, Neu5Gc, and 2-keto-3-deoxy-D-glycero-D-galacto-nononic acid (Kdn), and various internal glycan (GalβpNP and GalNAcβpNP). The Pd2,6ST S232L/T356S/W361F triple mutant was selective towards α2-6-linked sialic acid while retaining some promiscuity to the sialic acid form and internal glycan (FIG. 5, Table 5). For example, among Neu5Acα2-6/3/8GalβpNP (compounds 2-4), only Neu5Acα2-6GalβpNP (2) was a suitable substrate for the Pd2,6ST S232L/T356S/W361F. Activity toward Neu5Acα2-8GalβpNP (4) was not detected, and activity was nearly 400-fold lower toward Neu5Acα2-3GalβpNP (3) than Neu5Acα2-6GalβpNP (2), suggesting the high selectivity of the Pd2,6ST-derived neosialidase towards α2-6-sialyl linkage. The triple mutant was able to cleave α2-6-linked N-glycolylneuraminic acid (Neu5Gc) in Neu5Gcα2-6GalβpNP (6) at approximately 12% of the rate of Neu5Acα2-6GalβpNP (2), although Kdnα2-6GalβpNP (5) containing an α2-6-linked 2,3-dideoxy-2-keto-nonulosonic acid (Kdn) was cleaved at 0.1% of the rate of 2 and not a suitable substrate under the experimental conditions used. Quite interestingly, the neosialidase activity of the Pd2,6ST S232L/T356S/W361F triple mutant was higher towards Neu5Acα2-6GalNAcβpNP (7) than for Neu5Acα2-6GalβpNP (2).

TABLE 3

Kinetic parameters for Pd2,6ST mutant neosialidase activity in the presence of 0.5 mM CMP.

| Enzymes and mutants | $k_{cat}$ ($min^{-1}$) | $K_M$ (mM) | $k_{cat}/K_M$ ($min^{-1}mM^{-1}$) |
|---|---|---|---|
| Pd2,6ST[a] | 8.2 ± 0.3 | 7.6 ± 0.5 | 1.1 |
| Pd2,6ST W361F | 2.5 ± 0.2 | 1.0 ± 0.3 | 2.6 |
| Pd2,6ST S232L/W361F | 84 ± 4 | 1.1 ± 0.1 | 76 |
| Pd2,6ST S232L/T356S/W361F | (7.0 ± .2) × $10^2$ | 6.3 ± 0.2 | 1.1 × $10^2$ |
| hNEU2[b] | 10.8 ± 0.6 | 2.1 ± 0.2 | 5.1 |

[a]Reported previously. See, Cheng, Chen, et al. *Glycobiology* 2010, 20, 260-268

[b]Reported previously using Neu5Acα2-6GalβpNP as the substrate. See, Li, Chen, et al. *Mol. BioSyst.* 2011, 7, 1060-1072.

TABLE 4

Kinetic parameters for the CMP-Neu5Ac hydrolysis activities of Pd2,6ST and Pd2,6ST S232L/T356S/W361F neosialidase

| Enzyme and mutant | $k_{cat}$ ($min^{-1}$) | $K_M$ (mM) | $k_{cat}/K_m$ ($min^{-1}mM^{-1}$) |
|---|---|---|---|
| Pd2,6ST[a] | (4.0 ± 0.9) × $10^2$ | 45 ± 14 | 8.8 |
| Pd2,6ST S232L/T356S/W361F | (1.1 ± 0.01) × $10^4$ | 3.7 ± 0.1 | 3.0 × $10^3$ |

[a]Reported previously. McArthur, Chen, et al. See, *Org. Biomol. Chem.* 2017, 15, 1700-1709.

TABLE 5

Relative sialidase activities of Pd2,6ST S232L/T356S/W361F towards different sialosides.

| Compound number | Compound abbreviation | Relative sialidase activity |
|---|---|---|
| 2 | Neu5Acα2-6GalβpNP | 1.0 |
| 3 | Neu5Acα2-3GalβpNP | 2.5 × $10^{-3}$ |
| 4 | Neu5Acα2-8Neu5Acα2-3GalβpNP | 3.3 × $10^{-3}$ |
| 5 | Kdnα2-6GalβpNP | 9.8 × $10^{-4}$ |

TABLE 5-continued

| Relative sialidase activities of Pd2,6ST S232L/T356S/W361F towards different sialosides. | | |
|---|---|---|
| Compound number | Compound abbreviation | Relative sialidase activity |
| 6 | Neu5Gcα2-6GalβpNP | $1.2 \times 10^{-1}$ |
| 7 | Neu5Acα2-6GalNAcβpNP | 1.9 |

Example 5. Recognition of Egg Yolk Sialoglycopeptide

Figure 6:
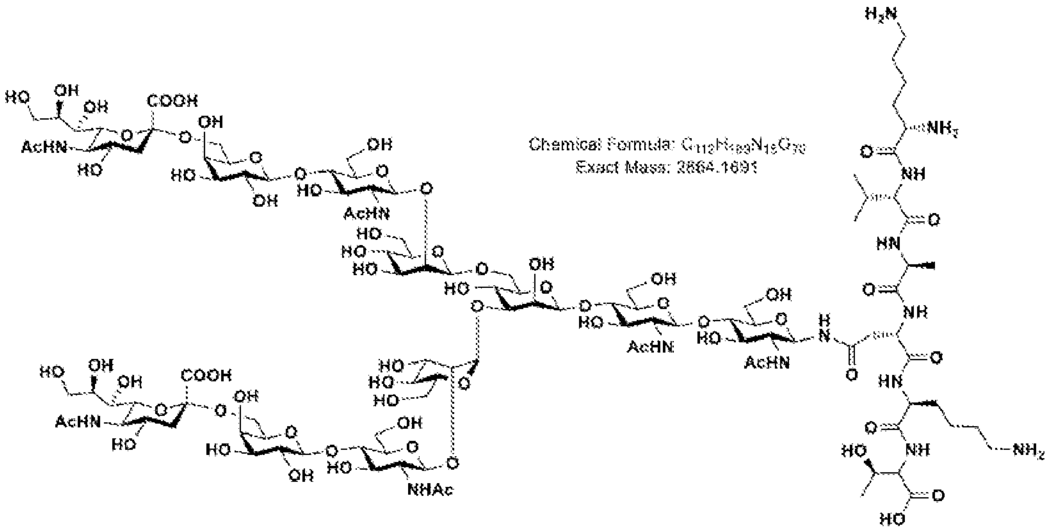
FIG. 6 shows the structure of egg yolk sialoglycopeptide (top) and related de-sialylated compounds.
Figure 6:
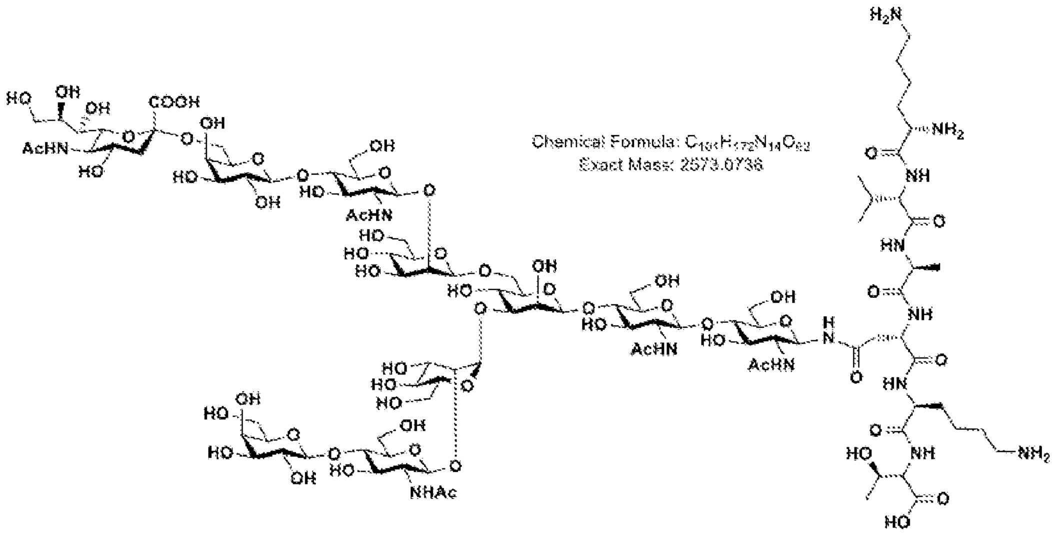
Figure 6:
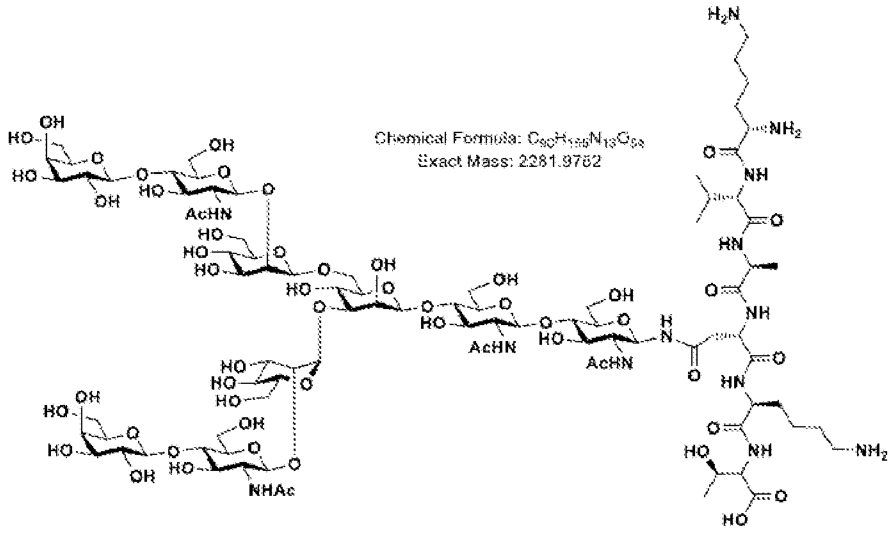

To demonstrate the utility of Pd2,6ST S232L/T356S/W361F toward more complex glycoconjugates, the neosialidase was tested against egg yolk sialoglycopeptide, a hexapeptide with a biantennary complex-type N-linked glycan containing α2-6-linked sialic acid on each antenna (FIG. 6). Reactions were performed at 37° C. for 60 min with MES buffer (100 mM, pH 6.0), $MgCl_2$ (10 mM), CMP (0.5 mM), Pd2,6ST S232L/T356S/W361F (0.0 or 13.0 μM), and egg yolk sialoglycopeptide (1 mM). Reactions were stopped by thermal denaturation of the enzyme at 60° C. for 10 min. The mixtures were incubated on ice for 30 min and centrifuged at 13,000 rpm for 5 min. Chromatographic separation and detection were achieved with an Infinity 1290-II HPLC equipped with a UV-vis detector (Agilent Technologies, CA). The HPLC procedure utilized a ZORBAX Bonus-RP Rapid Resolution HD 1.8 μm particle 2.1×100 mm column (Agilent Technologies, CA), a gradient flow of 0.7 mL $min^{-1}$ of 0.3 to 8% acetonitrile over 6 min in aqueous solution containing 0.1% TFA, and an injection volume of 1 μL. The peptide bond absorbance signal was monitored at 214 nm. High resolution (HR) electrospray ionization (ESI) mass spectra were obtained using a Thermo Electron LTQ-Orbitrap Hybrid MS at the Mass Spectrometry Facility in the University of California, Davis.

Detection of the de-sialylated glycopeptide by HPLC and high resolution mass spectrometry confirmed that the engineered neosialidase can recognize and cleave α2-6-linked sialic acid from complex sialylated glycoconjugates. Signals for (M+3)/2 ions were observed for the disialyl (Calcd. 1433.0924, found 1433.0910) in the no-enzyme control and asialo glycopeptides (Calcd. 1141.9969, found 1141.9967) in the neosialidase reaction. Monosialylated glycopeptide was not detected.

The reprogramming of natural enzymes for non-natural functions is an important area of interest for enzyme engineering. By exploiting the reversibility of glycosyltransferase activity and the evolvability of glycosyltransferase acceptor substrate promiscuity, we have demonstrated that glycosyltransferases can be conveniently engineered into efficient neoglycosidases with specificities not known to exist in nature. This strategy will likely provide a valuable source of new enzymes to supplement known exoglycosidases, particularly for the selective cleavage of sugars from natural product glycosides or complex carbohydrates.

The Pd2,6ST-derived neosialidase developed here catalyzes the removal of sialic acid with high selectivity toward α2-6-linkages and promiscuity toward Neu5Gc via a mechanism different from all known sialidase mechanisms. The engineered mutant will be a valuable addition to glycobiology, assisting in the elucidation of sialoglycan structure and function.

We were pleasantly surprised to discover three beneficial mutations across just six investigated residues within the active site of Pd2,6ST. This implies that the sialyltransferase activity of the enzyme is quite robust toward active site mutations and that the discrimination of nucleophilic water is quite sensitive to mutations. However, the Pd2,6ST triple mutant did not display the expected α2-6-sialidase activity toward Kdn even though Pd2,6ST was efficient in synthesizing Kdnα2-6-containing sialosides in high yield. This data suggests that the mutations that improved neosialidase toward Neu5Ac-containing probe Neu5Acα2-6GalβX (1) may have also altered the substrate specificity toward Kdn-containing compound Kdnα2-6GalβpNP (5).

In conclusion, Pd2,6ST S232L/T356S/W361F was generated by sequential saturation mutagenesis and screening using a high-throughput blue-white assay. This triple mutant displays over 100-fold improved catalytic efficiency relative to the wild-type while retaining linkage selectivity of the wild-type sialyltransferase activity. This enzyme is a useful new tool for studying the structure and function of sialoglycans, and the engineering strategy may be proven useful to researchers interested in obtaining enzymes with glycosidase specificities not already known to exist in nature.

Although the foregoing has been described in some detail by way of illustration and example for purposes of clarity and understanding, one of skill in the art will appreciate that certain changes and modifications can be practiced within the scope of the appended claims. All publications, patents, patent applications, and sequence accession numbers cited herein are hereby incorporated by reference in their entirety for all purposes.

V. INFORMAL SEQUENCE LISTING

```
(Pd2, 6ST; GenBank Accession No: BAA25316.1)
                                                  SEQ ID NO: 1
MKKILTVLSIFILSACNSDNTSLKETVSSNSADVVETETYQLTPIDAPSSFLSHSWEQTCGT

PILNESDKQAISFDFVAPELKQDEKYCFTFKGITGDHRYITNTTLTVVAPTLEVYIDHASLP

SLQQLIHIIQAKDEYPSNQRFVSWKRVTVDADNANKLNIHTYPLKGNNTSPEMVAAIDEYAQ

SKNRLNIEFYTNTAHVFNNLPPIIQPLYNNEKVKISHISLYDDGSSEYVSLYQWKDTPNKIE

TLEGEVSLLANYLAGTSPDAPKGMGNRYNWHKLYDTDYYFLREDYLDVEANLHDLRDYLGSS

AKQMPWDEFAKLSDSQQTLFLDIVGFDKEQLQQQYSQSPLPNFIFTGTTTWAGGETKEYYAQ

QQVNVINNAINETSPYYLGKDYDLFFKGHPAGGVINDIILGSFPDMINIPAKISFEVLMMTD

MLPDTVAGIASSLYFTIPADKVNFIVFTSSDTITDREEALKSPLVQVMLTLGIVKEKDVLFW

ADHKVNSMEVAIDEACTRIIAKRQPTASDLRLVIAIIKTITDLERIGDVAESIAKVALESFS
```

-continued

NKQYNLLVSLESLGQHTVRMLHEVLDAFARMDVKAAIEVYQEDDRIDQEYESIVRQLMAHMM

EDPSSIPNVMKVMWAARSIERVGDRCQNICEYIIYFVKGKDVRHTKPDDFGTMLD (Δ15Pd2, 6ST)

SEQ ID NO: 2

MGSSHHHHHHSSGLVPRGSHMCNSDNTSLKETVSSNSADVVETETYQLTPIDAPSSFLSHSW

EQTCGTPILNESDKQAISFDFVAPELKQDEKYCFTFKGITGDHRYITNTTLTVVAPTLEVYI

DHASLPSLQQLIHIIQAKDEYPSNQRFVSWKRVTVDADNANKLNIHTYPLKGNNTSPEMVAA

IDEYAQSKNRLNIEFYTNTAHVFNNLPPIIQPLYNNEKVKISHISLYDDGSSEYVSLYQWKD

TPNKIETLEGEVSLLANYLAGTSPDAPKGMGNRYNWHKLYDTDYYFLREDYLDVEANLHDLR

DYLGSSAKQMPWDEFAKLSDSQQTLFLDIVGFDKEQLQQQYSQSPLPNFIFTGTTTWAGGET

KEYYAQQQVNVINNAINETSPYYLGKDYDLFFKGHPAGGVINDIILGSFPDMINIPAKISFE

VLMMTDMLPDTVAGIASSLYFTIPADKVNFIVFTSSDTITDREEALKSPLVQVMLTLGIVKE

KDVLFWA (Δ16Psp2, 6ST)

SEQ ID NO: 3

MKNFLLLTLILLTACNNSEENTQSIIKNDINKTIIDEEYVNLEPINQSNISFTKHSWVQTCG

TQQLLTEQNKESISLSVVAPRLDDDEKYCFDFNGVSNKGEKYITKVTLNVVAPSLEVYVDHA

SLPTLQQLMDIIKSEEENPTAQRYIAWGRIVPTDEQMKELNITSFALINNHTPADLVQEIVK

QAQTKHRLNVKLSSNTAHSFDNLVPILKELNSFNNVTVTNIDLYDDGSAEYVNLYNWRDTLN

KTDNLKIGKDYLEDVINGINEDTSNTGTSSVYNWQKLYPANYHFLRKDYLTLEPSLHELRDY

IGDSLKQMQWDGFKKFNSKQQELFLSIVNFDKQKLQNEYNSSNLPNFVFTGTTVWAGNHERE

YYAKQQINVINNAINESSPHYLGNSYDLFFKGHPGGGIINTLIMQNYPSMVDIPSKISFEVL

MMTDMLPDAVAGIASSLYFTIPAEKIKFIVFTSTETITDRETALRSPLVQVMIKLGIVKEEN

VLFWADLPNCETGVCIAV (PmST1; PDB ID: 2IHZ)

SEQ ID NO: 4

MKNRRLNFKLFFLIIFSLFSTLSWSKTITLYLDPASLPALNQLMDFTQNNEDKTHPRIFGLS

RFKIPDNIITQYQNIHFVELKDNRPTEALFTILDQYPGNIELNIHLNIAHSVQLIRPILAYR

FKHLDRVSIQQLNLYDDGSMEYVDLEKEENKDISAEIKQAEKQLSHYLLTGKIKFDNPTIAR

YVWQSAFPVKYHFLSTDYFEKAEFLQPLKEYLAENYQKMDWTAYQQLTPEQQAFYLTLVGFN

DEVKQSLEVQQAKFIFTGTTTWEGNTDVREYYAQQQLNLLNHFTQAEGDLFIGDHYKIYFKG

HPRGGEINDYILNNAKNITNIPANISFEVLMMTGLLPDKVGGVASSLYFSLPKEKISHIIFT

SNKQVKSKEDALNNPYVKVMRRLGIIDESQVIFWDSLKQL (P.phosphoreum JT-ISH-467 α-/β-galactoside α-2,3-ST)

SEQ ID NO: 5

MFVFCKKIFFLIFISLMILGGCNSDSKHNNSDGNITKNKTIEVYVDRATLPTIQQMTQIINE

NSNNKKLISWSRYPINDETLLESINGSFFKNRPELIKSLDSMILTNEIKKVIINGNTLWAVD

VVNIIKSIEALGKKTEIELNFYDDGSAEYVRLYDFSRLPESEQEYKISLSKDNIQSSINGTQ

PFDNSIENIYGFSQLYPTTYHMLRADIFETNLPLTSLKRVISNNIKQMKWDYFTTFNSQQKN

KFYNFTGFNPEKIKEQYKASPHENFIFIGTNSGTATAEQQIDILTEAKKPDSPIITNSIQGL

DLFFKGHPSATYNQQIIDAHNMIEIYNKIPFEALIMTDALPDAVGGMGSSVFFSLPNTVENK

FIFYKSDTDIENNALIQVMIELNIVNRNDVKLISDLQ

What is claimed is:

1. An α2-6-sialyltransferase (2,6ST) variant having increased α2-6-specific sialidase catalytic efficiency ($k_{cat}/K_M$) as compared to a native 2,6ST, wherein the 2,6ST variant comprises an amino acid sequence having at least 90% amino acid sequence identity to the amino acid sequence of SEQ ID NO:2 and comprising one or more of:

a leucine residue at a position corresponding to residue 232 of SEQ ID NO: 1;

a serine residue at a position corresponding to residue 356 of SEQ ID NO: 1; and a phenylalanine residue at a position corresponding to residue 361 of SEQ ID NO: 1.

2. The 2,6ST variant of claim 1, wherein the 2,6ST variant comprises:

the leucine residue at the position corresponding to residue 232 of SEQ ID NO: 1;

the serine residue at the position corresponding to residue 356 of SEQ ID NO: 1; and the phenylalanine residue at the position corresponding to residue 361 of SEQ ID NO: 1.

3. The 2,6ST variant of claim 1, wherein the 2,6ST variant comprises an amino acid sequence having at least 95% sequence identity to the amino acid sequence of SEQ ID NO:2.

4. The 2,6ST variant of claim 1, wherein the 2,6ST variant comprises an amino acid sequence having at least 98% sequence identity to the amino acid sequence of SEQ ID NO:2.

5. An isolated nucleic acid encoding the 2,6ST variant according to claim 1.

6. A vector comprising the nucleic acid of claim 5.

7. An *Escherichia coli* host cell comprising the nucleic acid of claim 5.

* * * * *

SEQUENCE LISTING

<160> NUMBER OF SEQ ID NOS: 17

<210> SEQ ID NO 1
<211> LENGTH: 675
<212> TYPE: PRT
<213> ORGANISM: Photobacterium damselae

<400> SEQUENCE: 1

```
Met Lys Lys Ile Leu Thr Val Leu Ser Ile Phe Ile Leu Ser Ala Cys
1               5                   10                  15

Asn Ser Asp Asn Thr Ser Leu Lys Glu Thr Val Ser Ser Asn Ser Ala
            20                  25                  30

Asp Val Val Glu Thr Glu Thr Tyr Gln Leu Thr Pro Ile Asp Ala Pro
        35                  40                  45

Ser Ser Phe Leu Ser His Ser Trp Glu Gln Thr Cys Gly Thr Pro Ile
    50                  55                  60

Leu Asn Glu Ser Asp Lys Gln Ala Ile Ser Phe Asp Phe Val Ala Pro
65                  70                  75                  80

Glu Leu Lys Gln Asp Glu Lys Tyr Cys Phe Thr Phe Lys Gly Ile Thr
                85                  90                  95

Gly Asp His Arg Tyr Ile Thr Asn Thr Thr Leu Thr Val Val Ala Pro
            100                 105                 110

Thr Leu Glu Val Tyr Ile Asp His Ala Ser Leu Pro Ser Leu Gln Gln
        115                 120                 125

Leu Ile His Ile Ile Gln Ala Lys Asp Glu Tyr Pro Ser Asn Gln Arg
    130                 135                 140

Phe Val Ser Trp Lys Arg Val Thr Val Asp Ala Asp Asn Ala Asn Lys
145                 150                 155                 160

Leu Asn Ile His Thr Tyr Pro Leu Lys Gly Asn Asn Thr Ser Pro Glu
                165                 170                 175

Met Val Ala Ala Ile Asp Glu Tyr Ala Gln Ser Lys Asn Arg Leu Asn
            180                 185                 190

Ile Glu Phe Tyr Thr Asn Thr Ala His Val Phe Asn Asn Leu Pro Pro
        195                 200                 205

Ile Ile Gln Pro Leu Tyr Asn Asn Glu Lys Val Lys Ile Ser His Ile
    210                 215                 220

Ser Leu Tyr Asp Asp Gly Ser Ser Glu Tyr Val Ser Leu Tyr Gln Trp
225                 230                 235                 240

Lys Asp Thr Pro Asn Lys Ile Glu Thr Leu Glu Gly Glu Val Ser Leu
                245                 250                 255

Leu Ala Asn Tyr Leu Ala Gly Thr Ser Pro Asp Ala Pro Lys Gly Met
            260                 265                 270

Gly Asn Arg Tyr Asn Trp His Lys Leu Tyr Asp Thr Asp Tyr Tyr Phe
        275                 280                 285

Leu Arg Glu Asp Tyr Leu Asp Val Glu Ala Asn Leu His Asp Leu Arg
    290                 295                 300

Asp Tyr Leu Gly Ser Ser Ala Lys Gln Met Pro Trp Asp Glu Phe Ala
305                 310                 315                 320

Lys Leu Ser Asp Ser Gln Gln Thr Leu Phe Leu Asp Ile Val Gly Phe
                325                 330                 335

Asp Lys Glu Gln Leu Gln Gln Gln Tyr Ser Gln Ser Pro Leu Pro Asn
            340                 345                 350

Phe Ile Phe Thr Gly Thr Thr Thr Trp Ala Gly Gly Glu Thr Lys Glu
        355                 360                 365
```

-continued

Tyr Tyr Ala Gln Gln Gln Val Asn Val Ile Asn Asn Ala Ile Asn Glu
370 375 380

Thr Ser Pro Tyr Tyr Leu Gly Lys Asp Tyr Asp Leu Phe Phe Lys Gly
385 390 395 400

His Pro Ala Gly Gly Val Ile Asn Asp Ile Ile Leu Gly Ser Phe Pro
405 410 415

Asp Met Ile Asn Ile Pro Ala Lys Ile Ser Phe Glu Val Leu Met Met
420 425 430

Thr Asp Met Leu Pro Asp Thr Val Ala Gly Ile Ala Ser Ser Leu Tyr
435 440 445

Phe Thr Ile Pro Ala Asp Lys Val Asn Phe Ile Val Phe Thr Ser Ser
450 455 460

Asp Thr Ile Thr Asp Arg Glu Glu Ala Leu Lys Ser Pro Leu Val Gln
465 470 475 480

Val Met Leu Thr Leu Gly Ile Val Lys Glu Lys Asp Val Leu Phe Trp
485 490 495

Ala Asp His Lys Val Asn Ser Met Glu Val Ala Ile Asp Glu Ala Cys
500 505 510

Thr Arg Ile Ile Ala Lys Arg Gln Pro Thr Ala Ser Asp Leu Arg Leu
515 520 525

Val Ile Ala Ile Ile Lys Thr Ile Thr Asp Leu Glu Arg Ile Gly Asp
530 535 540

Val Ala Glu Ser Ile Ala Lys Val Ala Leu Glu Ser Phe Ser Asn Lys
545 550 555 560

Gln Tyr Asn Leu Leu Val Ser Leu Glu Ser Leu Gly Gln His Thr Val
565 570 575

Arg Met Leu His Glu Val Leu Asp Ala Phe Ala Arg Met Asp Val Lys
580 585 590

Ala Ala Ile Glu Val Tyr Gln Glu Asp Asp Arg Ile Asp Gln Glu Tyr
595 600 605

Glu Ser Ile Val Arg Gln Leu Met Ala His Met Met Glu Asp Pro Ser
610 615 620

Ser Ile Pro Asn Val Met Lys Val Met Trp Ala Ala Arg Ser Ile Glu
625 630 635 640

Arg Val Gly Asp Arg Cys Gln Asn Ile Cys Glu Tyr Ile Ile Tyr Phe
645 650 655

Val Lys Gly Lys Asp Val Arg His Thr Lys Pro Asp Asp Phe Gly Thr
660 665 670

Met Leu Asp
675

<210> SEQ ID NO 2
<211> LENGTH: 503
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2

Met Gly Ser Ser His His His His His His Ser Ser Gly Leu Val Pro
1 5 10 15

Arg Gly Ser His Met Cys Asn Ser Asp Asn Thr Ser Leu Lys Glu Thr
20 25 30

Val Ser Ser Asn Ser Ala Asp Val Val Glu Thr Glu Thr Tyr Gln Leu
35 40 45

-continued

```
Thr Pro Ile Asp Ala Pro Ser Ser Phe Leu Ser His Ser Trp Glu Gln
    50                  55                  60

Thr Cys Gly Thr Pro Ile Leu Asn Glu Ser Asp Lys Gln Ala Ile Ser
65                  70                  75                  80

Phe Asp Phe Val Ala Pro Glu Leu Lys Gln Asp Glu Lys Tyr Cys Phe
                85                  90                  95

Thr Phe Lys Gly Ile Thr Gly Asp His Arg Tyr Ile Thr Asn Thr Thr
            100                 105                 110

Leu Thr Val Val Ala Pro Thr Leu Glu Val Tyr Ile Asp His Ala Ser
        115                 120                 125

Leu Pro Ser Leu Gln Gln Leu Ile His Ile Ile Gln Ala Lys Asp Glu
    130                 135                 140

Tyr Pro Ser Asn Gln Arg Phe Val Ser Trp Lys Arg Val Thr Val Asp
145                 150                 155                 160

Ala Asp Asn Ala Asn Lys Leu Asn Ile His Thr Tyr Pro Leu Lys Gly
                165                 170                 175

Asn Asn Thr Ser Pro Glu Met Val Ala Ala Ile Asp Glu Tyr Ala Gln
            180                 185                 190

Ser Lys Asn Arg Leu Asn Ile Glu Phe Tyr Thr Asn Thr Ala His Val
        195                 200                 205

Phe Asn Asn Leu Pro Pro Ile Ile Gln Pro Leu Tyr Asn Asn Glu Lys
    210                 215                 220

Val Lys Ile Ser His Ile Ser Leu Tyr Asp Asp Gly Ser Ser Glu Tyr
225                 230                 235                 240

Val Ser Leu Tyr Gln Trp Lys Asp Thr Pro Asn Lys Ile Glu Thr Leu
                245                 250                 255

Glu Gly Glu Val Ser Leu Leu Ala Asn Tyr Leu Ala Gly Thr Ser Pro
            260                 265                 270

Asp Ala Pro Lys Gly Met Gly Asn Arg Tyr Asn Trp His Lys Leu Tyr
        275                 280                 285

Asp Thr Asp Tyr Tyr Phe Leu Arg Glu Asp Tyr Leu Asp Val Glu Ala
    290                 295                 300

Asn Leu His Asp Leu Arg Asp Tyr Leu Gly Ser Ser Ala Lys Gln Met
305                 310                 315                 320

Pro Trp Asp Glu Phe Ala Lys Leu Ser Asp Ser Gln Gln Thr Leu Phe
                325                 330                 335

Leu Asp Ile Val Gly Phe Asp Lys Glu Gln Leu Gln Gln Gln Tyr Ser
            340                 345                 350

Gln Ser Pro Leu Pro Asn Phe Ile Phe Thr Gly Thr Thr Thr Trp Ala
        355                 360                 365

Gly Gly Glu Thr Lys Glu Tyr Tyr Ala Gln Gln Gln Val Asn Val Ile
    370                 375                 380

Asn Asn Ala Ile Asn Glu Thr Ser Pro Tyr Tyr Leu Gly Lys Asp Tyr
385                 390                 395                 400

Asp Leu Phe Phe Lys Gly His Pro Ala Gly Gly Val Ile Asn Asp Ile
                405                 410                 415

Ile Leu Gly Ser Phe Pro Asp Met Ile Asn Ile Pro Ala Lys Ile Ser
            420                 425                 430

Phe Glu Val Leu Met Met Thr Asp Met Leu Pro Asp Thr Val Ala Gly
        435                 440                 445

Ile Ala Ser Ser Leu Tyr Phe Thr Ile Pro Ala Asp Lys Val Asn Phe
    450                 455                 460
```

-continued

Ile Val Phe Thr Ser Ser Asp Thr Ile Thr Asp Arg Glu Glu Ala Leu
465 470 475 480

Lys Ser Pro Leu Val Gln Val Met Leu Thr Leu Gly Ile Val Lys Glu
485 490 495

Lys Asp Val Leu Phe Trp Ala
500

<210> SEQ ID NO 3
<211> LENGTH: 514
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

Met Lys Asn Phe Leu Leu Leu Thr Leu Ile Leu Leu Thr Ala Cys Asn
1 5 10 15

Asn Ser Glu Glu Asn Thr Gln Ser Ile Ile Lys Asn Asp Ile Asn Lys
20 25 30

Thr Ile Ile Asp Glu Glu Tyr Val Asn Leu Glu Pro Ile Asn Gln Ser
35 40 45

Asn Ile Ser Phe Thr Lys His Ser Trp Val Gln Thr Cys Gly Thr Gln
50 55 60

Gln Leu Leu Thr Glu Gln Asn Lys Glu Ser Ile Ser Leu Ser Val Val
65 70 75 80

Ala Pro Arg Leu Asp Asp Asp Glu Lys Tyr Cys Phe Asp Phe Asn Gly
85 90 95

Val Ser Asn Lys Gly Glu Lys Tyr Ile Thr Lys Val Thr Leu Asn Val
100 105 110

Val Ala Pro Ser Leu Glu Val Tyr Val Asp His Ala Ser Leu Pro Thr
115 120 125

Leu Gln Gln Leu Met Asp Ile Ile Lys Ser Glu Glu Glu Asn Pro Thr
130 135 140

Ala Gln Arg Tyr Ile Ala Trp Gly Arg Ile Val Pro Thr Asp Glu Gln
145 150 155 160

Met Lys Glu Leu Asn Ile Thr Ser Phe Ala Leu Ile Asn Asn His Thr
165 170 175

Pro Ala Asp Leu Val Gln Glu Ile Val Lys Gln Ala Gln Thr Lys His
180 185 190

Arg Leu Asn Val Lys Leu Ser Ser Asn Thr Ala His Ser Phe Asp Asn
195 200 205

Leu Val Pro Ile Leu Lys Glu Leu Asn Ser Phe Asn Asn Val Thr Val
210 215 220

Thr Asn Ile Asp Leu Tyr Asp Asp Gly Ser Ala Glu Tyr Val Asn Leu
225 230 235 240

Tyr Asn Trp Arg Asp Thr Leu Asn Lys Thr Asp Asn Leu Lys Ile Gly
245 250 255

Lys Asp Tyr Leu Glu Asp Val Ile Asn Gly Ile Asn Glu Asp Thr Ser
260 265 270

Asn Thr Gly Thr Ser Ser Val Tyr Asn Trp Gln Lys Leu Tyr Pro Ala
275 280 285

Asn Tyr His Phe Leu Arg Lys Asp Tyr Leu Thr Leu Glu Pro Ser Leu
290 295 300

His Glu Leu Arg Asp Tyr Ile Gly Asp Ser Leu Lys Gln Met Gln Trp
305 310 315 320

```
Asp Gly Phe Lys Lys Phe Asn Ser Lys Gln Gln Glu Leu Phe Leu Ser
                325                 330                 335

Ile Val Asn Phe Asp Lys Gln Lys Leu Gln Asn Glu Tyr Asn Ser Ser
            340                 345                 350

Asn Leu Pro Asn Phe Val Phe Thr Gly Thr Thr Val Trp Ala Gly Asn
        355                 360                 365

His Glu Arg Glu Tyr Tyr Ala Lys Gln Gln Ile Asn Val Ile Asn Asn
    370                 375                 380

Ala Ile Asn Glu Ser Ser Pro His Tyr Leu Gly Asn Ser Tyr Asp Leu
385                 390                 395                 400

Phe Phe Lys Gly His Pro Gly Gly Gly Ile Ile Asn Thr Leu Ile Met
                405                 410                 415

Gln Asn Tyr Pro Ser Met Val Asp Ile Pro Ser Lys Ile Ser Phe Glu
            420                 425                 430

Val Leu Met Met Thr Asp Met Leu Pro Asp Ala Val Ala Gly Ile Ala
        435                 440                 445

Ser Ser Leu Tyr Phe Thr Ile Pro Ala Glu Lys Ile Lys Phe Ile Val
    450                 455                 460

Phe Thr Ser Thr Glu Thr Ile Thr Asp Arg Glu Thr Ala Leu Arg Ser
465                 470                 475                 480

Pro Leu Val Gln Val Met Ile Lys Leu Gly Ile Val Lys Glu Glu Asn
                485                 490                 495

Val Leu Phe Trp Ala Asp Leu Pro Asn Cys Glu Thr Gly Val Cys Ile
            500                 505                 510

Ala Val


<210> SEQ ID NO 4
<211> LENGTH: 412
<212> TYPE: PRT
<213> ORGANISM: Pasteurella multocida

<400> SEQUENCE: 4

Met Lys Asn Arg Arg Leu Asn Phe Lys Leu Phe Phe Leu Ile Ile Phe
1               5                   10                  15

Ser Leu Phe Ser Thr Leu Ser Trp Ser Lys Thr Ile Thr Leu Tyr Leu
            20                  25                  30

Asp Pro Ala Ser Leu Pro Ala Leu Asn Gln Leu Met Asp Phe Thr Gln
        35                  40                  45

Asn Asn Glu Asp Lys Thr His Pro Arg Ile Phe Gly Leu Ser Arg Phe
    50                  55                  60

Lys Ile Pro Asp Asn Ile Ile Thr Gln Tyr Gln Asn Ile His Phe Val
65                  70                  75                  80

Glu Leu Lys Asp Asn Arg Pro Thr Glu Ala Leu Phe Thr Ile Leu Asp
                85                  90                  95

Gln Tyr Pro Gly Asn Ile Glu Leu Asn Ile His Leu Asn Ile Ala His
            100                 105                 110

Ser Val Gln Leu Ile Arg Pro Ile Leu Ala Tyr Arg Phe Lys His Leu
        115                 120                 125

Asp Arg Val Ser Ile Gln Gln Leu Asn Leu Tyr Asp Asp Gly Ser Met
    130                 135                 140

Glu Tyr Val Asp Leu Glu Lys Glu Glu Asn Lys Asp Ile Ser Ala Glu
145                 150                 155                 160

Ile Lys Gln Ala Glu Lys Gln Leu Ser His Tyr Leu Leu Thr Gly Lys
                165                 170                 175
```

-continued

```
Ile Lys Phe Asp Asn Pro Thr Ile Ala Arg Tyr Val Trp Gln Ser Ala
            180                 185                 190

Phe Pro Val Lys Tyr His Phe Leu Ser Thr Asp Tyr Phe Glu Lys Ala
        195                 200                 205

Glu Phe Leu Gln Pro Leu Lys Glu Tyr Leu Ala Glu Asn Tyr Gln Lys
    210                 215                 220

Met Asp Trp Thr Ala Tyr Gln Gln Leu Thr Pro Glu Gln Gln Ala Phe
225                 230                 235                 240

Tyr Leu Thr Leu Val Gly Phe Asn Asp Glu Val Lys Gln Ser Leu Glu
                245                 250                 255

Val Gln Gln Ala Lys Phe Ile Phe Thr Gly Thr Thr Thr Trp Glu Gly
            260                 265                 270

Asn Thr Asp Val Arg Glu Tyr Tyr Ala Gln Gln Gln Leu Asn Leu Leu
        275                 280                 285

Asn His Phe Thr Gln Ala Glu Gly Asp Leu Phe Ile Gly Asp His Tyr
    290                 295                 300

Lys Ile Tyr Phe Lys Gly His Pro Arg Gly Gly Glu Ile Asn Asp Tyr
305                 310                 315                 320

Ile Leu Asn Asn Ala Lys Asn Ile Thr Asn Ile Pro Ala Asn Ile Ser
                325                 330                 335

Phe Glu Val Leu Met Met Thr Gly Leu Leu Pro Asp Lys Val Gly Gly
            340                 345                 350

Val Ala Ser Ser Leu Tyr Phe Ser Leu Pro Lys Glu Lys Ile Ser His
        355                 360                 365

Ile Ile Phe Thr Ser Asn Lys Gln Val Lys Ser Lys Glu Asp Ala Leu
    370                 375                 380

Asn Asn Pro Tyr Val Lys Val Met Arg Arg Leu Gly Ile Ile Asp Glu
385                 390                 395                 400

Ser Gln Val Ile Phe Trp Asp Ser Leu Lys Gln Leu
                405                 410


<210> SEQ ID NO 5
<211> LENGTH: 409
<212> TYPE: PRT
<213> ORGANISM: Photobacterium phosphoreum

<400> SEQUENCE: 5

Met Phe Val Phe Cys Lys Lys Ile Phe Phe Leu Ile Phe Ile Ser Leu
1               5                   10                  15

Met Ile Leu Gly Gly Cys Asn Ser Asp Ser Lys His Asn Asn Ser Asp
            20                  25                  30

Gly Asn Ile Thr Lys Asn Lys Thr Ile Glu Val Tyr Val Asp Arg Ala
        35                  40                  45

Thr Leu Pro Thr Ile Gln Gln Met Thr Gln Ile Ile Asn Glu Asn Ser
    50                  55                  60

Asn Asn Lys Lys Leu Ile Ser Trp Ser Arg Tyr Pro Ile Asn Asp Glu
65                  70                  75                  80

Thr Leu Leu Glu Ser Ile Asn Gly Ser Phe Phe Lys Asn Arg Pro Glu
                85                  90                  95

Leu Ile Lys Ser Leu Asp Ser Met Ile Leu Thr Asn Glu Ile Lys Lys
            100                 105                 110

Val Ile Ile Asn Gly Asn Thr Leu Trp Ala Val Asp Val Val Asn Ile
        115                 120                 125

Ile Lys Ser Ile Glu Ala Leu Gly Lys Lys Thr Glu Ile Glu Leu Asn
```

-continued

```
    130                 135                 140

Phe Tyr Asp Asp Gly Ser Ala Glu Tyr Val Arg Leu Tyr Asp Phe Ser
145                 150                 155                 160

Arg Leu Pro Glu Ser Glu Gln Glu Tyr Lys Ile Ser Leu Ser Lys Asp
                165                 170                 175

Asn Ile Gln Ser Ser Ile Asn Gly Thr Gln Pro Phe Asp Asn Ser Ile
            180                 185                 190

Glu Asn Ile Tyr Gly Phe Ser Gln Leu Tyr Pro Thr Thr Tyr His Met
        195                 200                 205

Leu Arg Ala Asp Ile Phe Glu Thr Asn Leu Pro Leu Thr Ser Leu Lys
    210                 215                 220

Arg Val Ile Ser Asn Asn Ile Lys Gln Met Lys Trp Asp Tyr Phe Thr
225                 230                 235                 240

Thr Phe Asn Ser Gln Gln Lys Asn Lys Phe Tyr Asn Phe Thr Gly Phe
                245                 250                 255

Asn Pro Glu Lys Ile Lys Glu Gln Tyr Lys Ala Ser Pro His Glu Asn
            260                 265                 270

Phe Ile Phe Ile Gly Thr Asn Ser Gly Thr Ala Thr Ala Glu Gln Gln
        275                 280                 285

Ile Asp Ile Leu Thr Glu Ala Lys Lys Pro Asp Ser Pro Ile Ile Thr
    290                 295                 300

Asn Ser Ile Gln Gly Leu Asp Leu Phe Phe Lys Gly His Pro Ser Ala
305                 310                 315                 320

Thr Tyr Asn Gln Gln Ile Ile Asp Ala His Asn Met Ile Glu Ile Tyr
                325                 330                 335

Asn Lys Ile Pro Phe Glu Ala Leu Ile Met Thr Asp Ala Leu Pro Asp
            340                 345                 350

Ala Val Gly Gly Met Gly Ser Ser Val Phe Phe Ser Leu Pro Asn Thr
        355                 360                 365

Val Glu Asn Lys Phe Ile Phe Tyr Lys Ser Asp Thr Asp Ile Glu Asn
    370                 375                 380

Asn Ala Leu Ile Gln Val Met Ile Glu Leu Asn Ile Val Asn Arg Asn
385                 390                 395                 400

Asp Val Lys Leu Ile Ser Asp Leu Gln
                405


<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(2)
<223> OTHER INFORMATION: a, c, t, g, unknown or other

<400> SEQUENCE: 6

nnkggttctt ctgaatatgt aagtttatat caatgg                              36


<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 7
atcatacaaa ctaatatgag aaattttcac cttctcg 37

<210> SEQ ID NO 8
<211> LENGTH: 71
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (35)..(36)
<223> OTHER INFORMATION: a, c, t, g, unknown or other

<400> SEQUENCE: 8
aatttctcat attagtttgt atgatgatgg ttctnnkgaa tatgtaagtt tatatcaatg 60
gaaagataca c 71

<210> SEQ ID NO 9
<211> LENGTH: 71
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (36)..(37)
<223> OTHER INFORMATION: a, c, t, g, unknown or other

<400> SEQUENCE: 9
gtgtatcttt ccattgatat aaacttacat attcmnnaga accatcatca tacaaactaa 60
tatgagaaat t 71

<210> SEQ ID NO 10
<211> LENGTH: 59
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (38)..(39)
<223> OTHER INFORMATION: a, c, t, g, unknown or other

<400> SEQUENCE: 10
acaatattca caatccccac taccaaactt tatttttnnk ggcacaacaa cttttgctg 59

<210> SEQ ID NO 11
<211> LENGTH: 59
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (21)..(22)
<223> OTHER INFORMATION: a, c, t, g, unknown or other

<400> SEQUENCE: 11
cagcaaaagt tgttgtgccm nnaaaaataa agtttggtag tggggattgt gaatattgt 59

<210> SEQ ID NO 12
<211> LENGTH: 18

<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (1)..(2)
<223> OTHER INFORMATION: a, c, t, g, unknown or other

<400> SEQUENCE: 12
nnkgctgggg gggaaacg 18

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 13
agttgttgtg ccggtaaaaa taaagtttgg 30

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (31)..(32)
<223> OTHER INFORMATION: a, c, t, g, unknown or other

<400> SEQUENCE: 14
gactacgatc tatttttcaa ggggcatcct nnkggtggcg ttattaacg 49

<210> SEQ ID NO 15
<211> LENGTH: 49
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (18)..(19)
<223> OTHER INFORMATION: a, c, t, g, unknown or other

<400> SEQUENCE: 15
cgttaataac gccaccmnna ggatgcccct tgaaaaatag atcgtagtc 49

<210> SEQ ID NO 16
<211> LENGTH: 53
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (26)..(27)
<223> OTHER INFORMATION: a, c, t, g, unknown or other

<400> SEQUENCE: 16
tgatatgatc aatattccag ccaagnnktc atttgaggtc ttgatgatga cgg 53

-continued

```
<210> SEQ ID NO 17
<211> LENGTH: 53
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (27)..(28)
<223> OTHER INFORMATION: a, c, t, g, unknown or other

<400> SEQUENCE: 17

ccgtcatcat caagacctca aatgamnnct tggctggaat attgatcata tca          53
```